United States Patent [19]

Takasugi et al.

[11] Patent Number: 5,512,588
[45] Date of Patent: Apr. 30, 1996

[54] FURYLTHIAZOLES AND THEIR USE AS $H_2$-RECEPTOR ANTAGONISTS AND ANTIMICROBIALS

[75] Inventors: Hisashi Takasugi, Sakai; Yousuke Katsura, Toyonaka; Yoshikazu Inoue, Amagasaki; Tetsuo Tomishi, Minoo, all of Japan

[73] Assignee: Fujisawa Pharmaceutical Co., Ltd., Osaka, Japan

[21] Appl. No.: 182,119

[22] PCT Filed: Aug. 3, 1992

[86] PCT No.: PCT/JP92/00986

§ 371 Date: Jan. 28, 1994

§ 102(e) Date: Jan. 28, 1994

[87] PCT Pub. No.: WO93/03028

PCT Pub. Date: Feb. 18, 1993

[30] Foreign Application Priority Data

Aug. 2, 1991 [GB] United Kingdom .................... 9116736
Apr. 22, 1992 [GB] United Kingdom .................... 9208734

[51] Int. Cl.$^6$ ................ G07D 417/04; A61K 31/425
[52] U.S. Cl. .................. 514/370; 514/342; 546/280; 548/139; 548/193; 548/194
[58] Field of Search ................... 548/193, 194; 546/280; 514/370, 342

[56] References Cited

U.S. PATENT DOCUMENTS 5,308,857  5/1994  Takasugi ................. 514/370

Primary Examiner—Robert Gerstl
Attorney, Agent, or Firm—Oblon, Spivak, McClelland, Maier & Neustadt

[57] ABSTRACT

This invention relates to furylthiazole derivatives represented by the following formula:

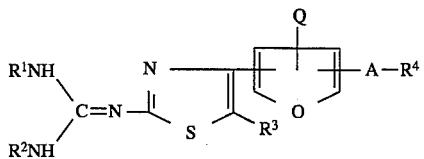

wherein each symbol is as defined in the specification and pharmaceutically acceptable salts thereof which have anti-ulcer activity, $H_2$-receptor antagonism and antimicrobial activity, to processes for the preparation thereof, to a pharmaceutical composition comprising the same and to a method for the treatment of ulcer and infectious diseases in human being or animals.

8 Claims, No Drawings

FURYLTHIAZOLES AND THEIR USE AS $H_2$-RECEPTOR ANTAGONISTS AND ANTIMICROBIALS

This application is a 371 of PCT/JP92/00986 filed Aug. 3, 1992.

TECHNICAL FIELD

This invention relates to new furylthiazole derivatives and pharmaceutically acceptable salts thereof.

More particularly, it relates to furylthiazole derivatives and pharmaceutically acceptable salts thereof which have antiulcer activity, $H_2$-receptor antagonism and antimicrobial activity, to processes for the preparation thereof, to a pharmaceutical composition comprising the same and to a method for the treatment of ulcer and infectious diseases in human being or animals.

BACKGROUND ART

In European Patent Application Publication No. 355,612, there are disclosed furylthiazole derivatives having antiulcer activity and $H_2$-receptor antagonism.

DISCLOSURE OF THE INVENTION

One object of this invention is to provide new furylthiazole derivatives and pharmaceutically acceptable salts thereof which possess antiulcer activity, $H_2$-receptor antagonism and antimicrobial activity.

Another object of this invention is to provide processes for the preparation of said furylthiazole derivatives and salt thereof.

A further object of this invention is to provide a pharmaceutical composition comprising, as an active ingredient, said furylthiazole derivatives or pharmaceutically acceptable salts thereof.

Still further object of this invention is to provide a therapeutical method for the treatment of ulcer and infectious diseases in human being or animals.

The furylthiazole derivatives of this invention are new and can be represented by the following general formula (I):

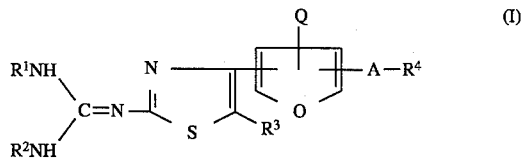

wherein
$R^1$ is methyl, ethyl, propyl, butyl, hexyl, lower alkoxy(lower)alkyl, lower alkenyl, lower alkynyl, cyclo(lower)alkyl, heterocyclic(lower)alkyl or hydroxy(lower)alkyl,
$R^2$ is hydrogen,
$R^3$ is hydrogen or lower alkyl,
$R^4$ is amino, acyl, acylamino, lower alkylisothioureido, heterocyclic amino, heterocyclic group, or a group of the formula:

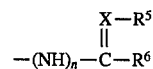

in which n is 0 or 1,
X is =CH— or =N—,
$R^5$ is hydrogen, cyano, nitro or acyl, and
$R^6$ is hydrogen, lower alkyl, lower alkylthio, lower alkoxy or amino which may have suitable substituent(s), and
A is lower alkylene or —CONH—; or
A—$R^4$ is heterocyclic group, and
Q is hydrogen or lower alkyl,
provided that when $R^1$ is methyl,
then $R^4$ is amino, lower alkanoylamino or a group of the formula:

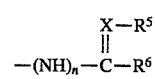

in which n, X, $R^5$ and $R^6$ are each as defined above.

The object compound (I) or a salt thereof can be prepared by processes as illustrated in the following reaction schemes.

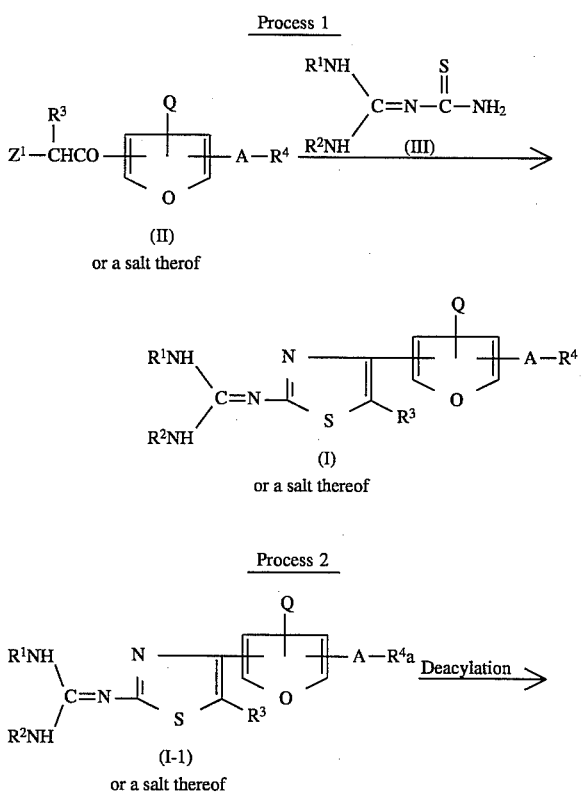

3
-continued
Process 2
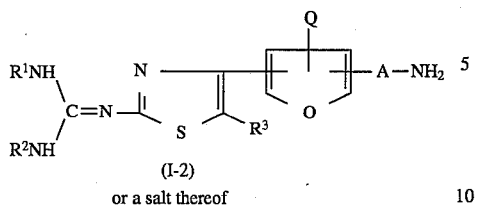
(I-2)
or a salt thereof
Process 3
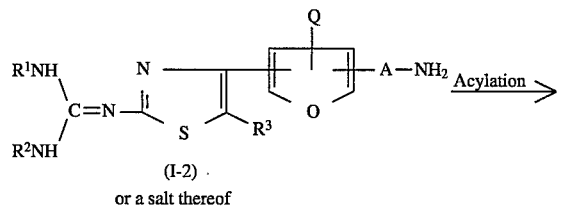
(I-2)
or a salt thereof
4
-continued
Process 3
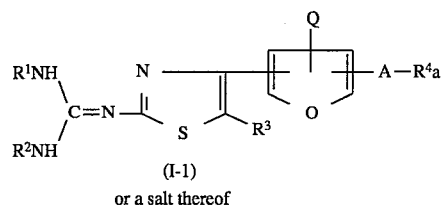
(I-1)
or a salt thereof
Process 4
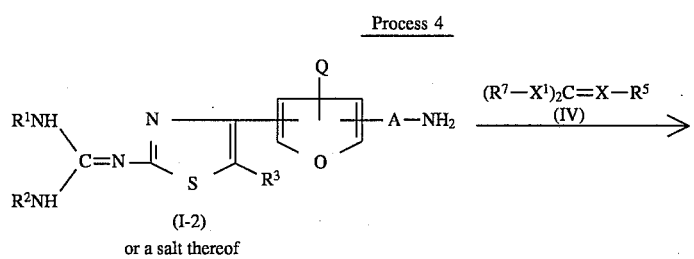
(I-2)
or a salt thereof
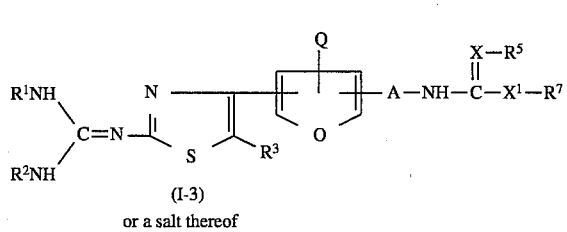
(I-3)
or a salt thereof
Process 5
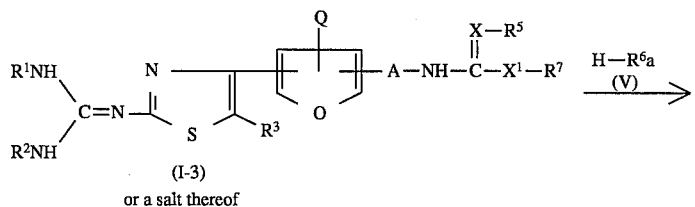
(I-3)
or a salt thereof
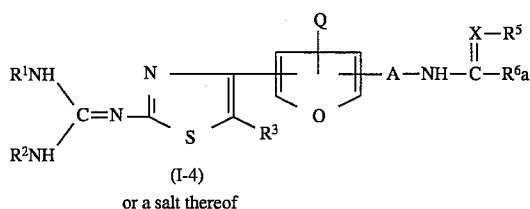
(I-4)
or a salt thereof Process 6
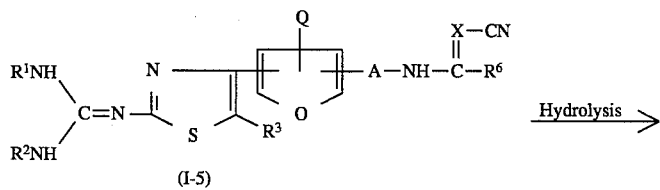
(I-5)
or a salt thereof
Hydrolysis →
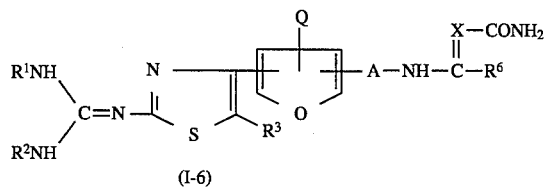
(I-6)
or a salt thereof
Process 7
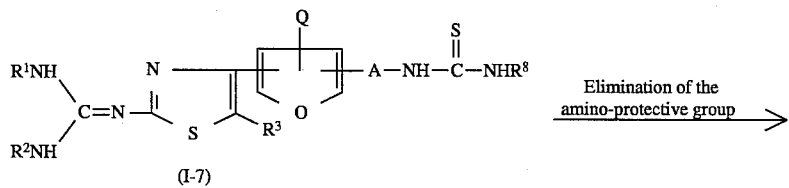
(I-7)
or a salt thereof
Elimination of the amino-protective group →
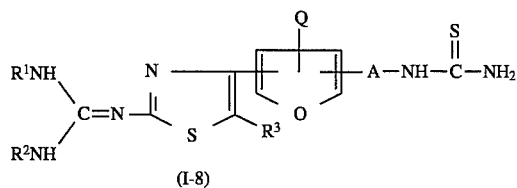
(I-8)
or a salt thereof
Process 8
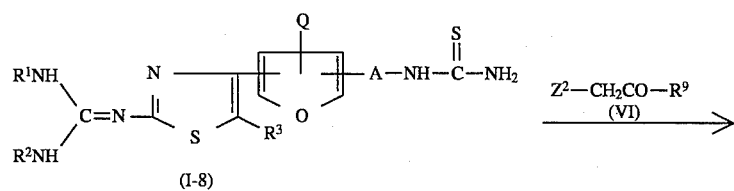
(I-8)
or a salt thereof
$Z^2-CH_2CO-R^9$
(VI)
→

-continued
Process 8
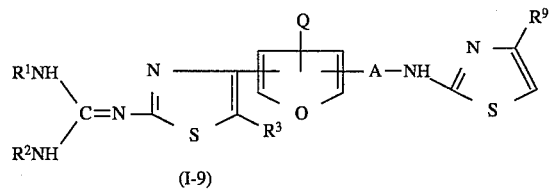
(I-9)
or a salt thereof
Process 9
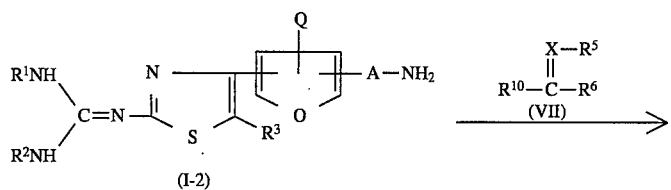
(I-2)
or a salt thereof
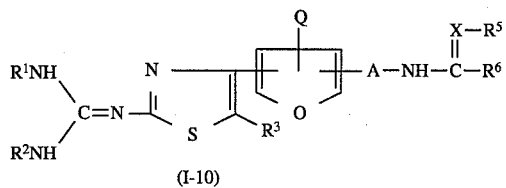
(I-10)
or a salt thereof
Process 10
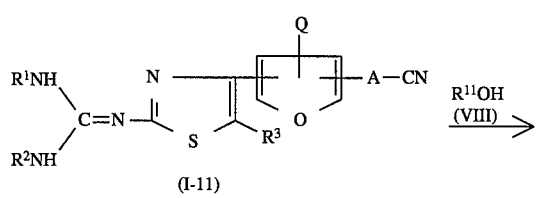
(I-11)
or a salt thereof
-continued
Process 10
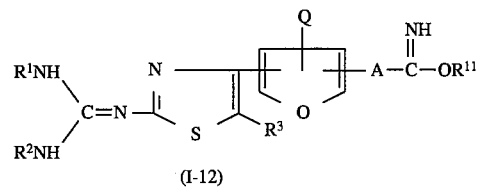
(I-12)
or a salt thereof
Process 11
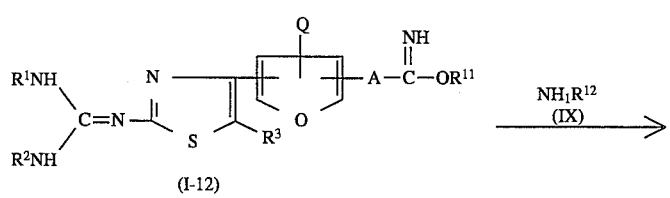
(I-12)
or a salt thereof -continued
Process 11
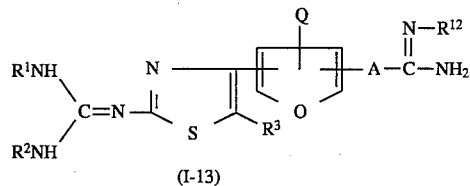
(I-13)
or a salt thereof
Process 12
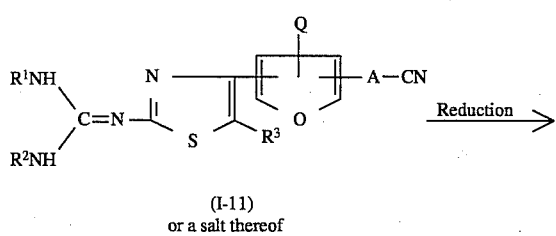
(I-11)
or a salt thereof
Process 14
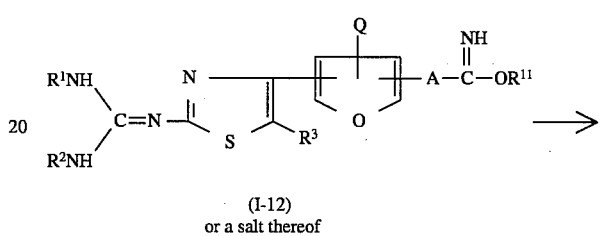
(I-12)
or a salt thereof
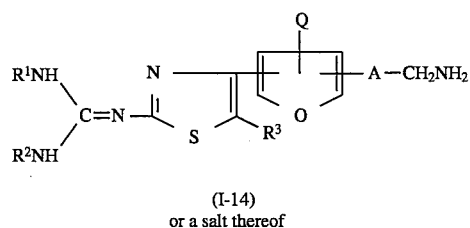
(I-14)
or a salt thereof
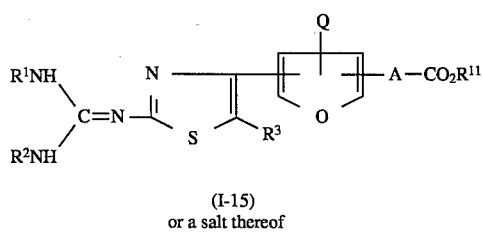
(I-15)
or a salt thereof
Process 13
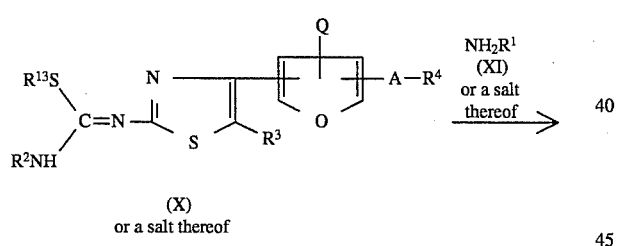
(X)
or a salt thereof
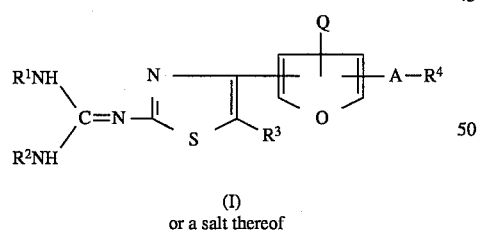
(I)
or a salt thereof

Process 15
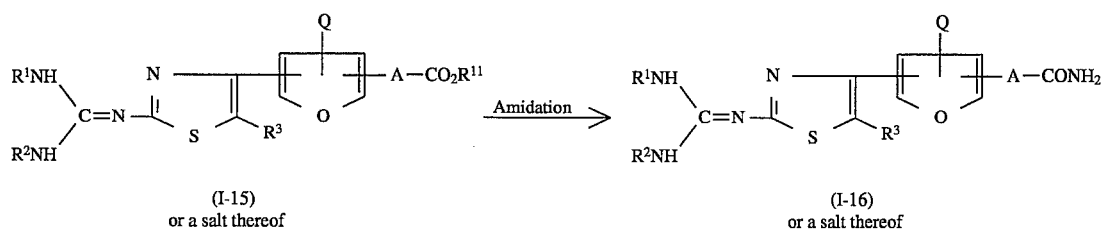
(I-15) or a salt thereof → (I-16) or a salt thereof
Process 16
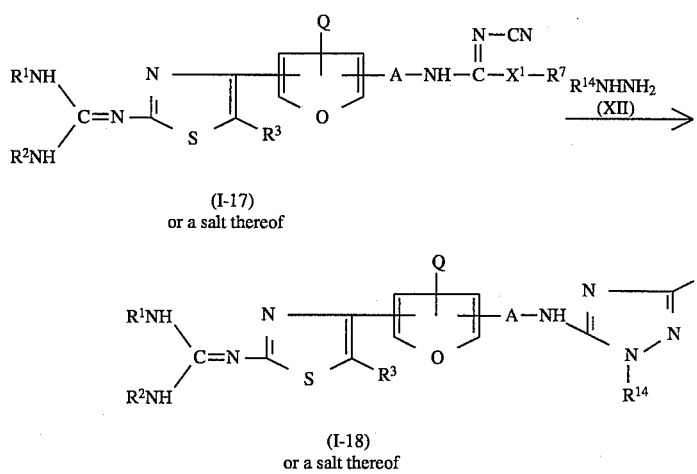
(I-17) or a salt thereof
(I-18) or a salt thereof
Process 17
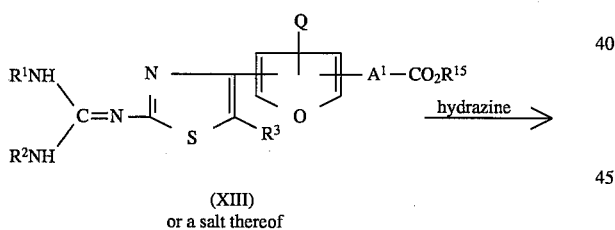
(XIII) or a salt thereof
-continued
Process 17
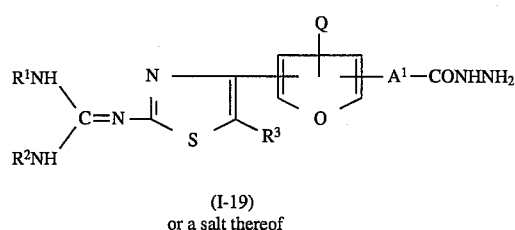
(I-19) or a salt thereof
Process 18
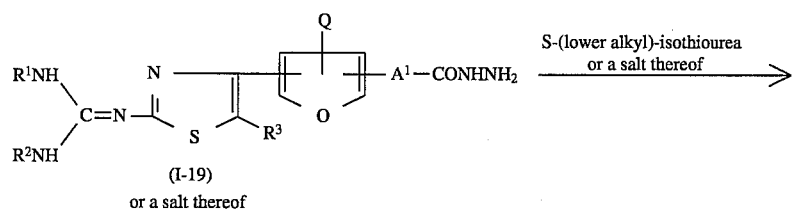
(I-19) or a salt thereof -continued
Process 18
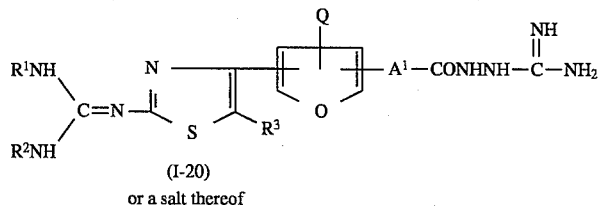
(I-20)
or a salt thereof
Process 19
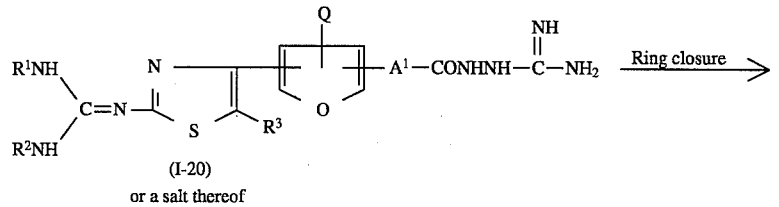
(I-20)
or a salt thereof
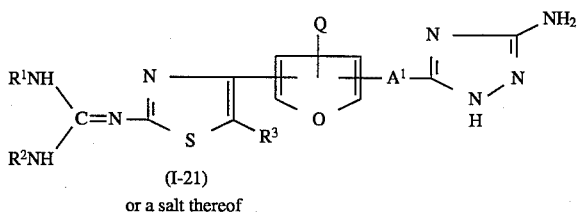
(I-21)
or a salt thereof
Process 20
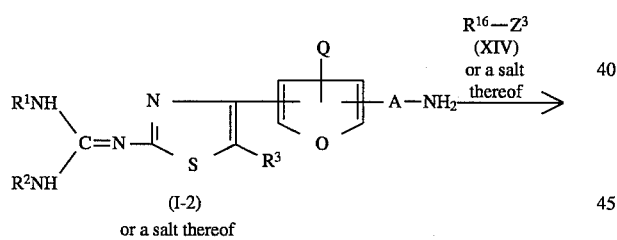
(I-2)
or a salt thereof
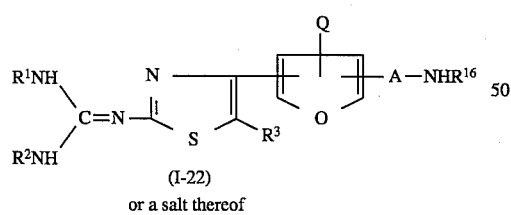
(I-22)
or a salt thereof
Process 21
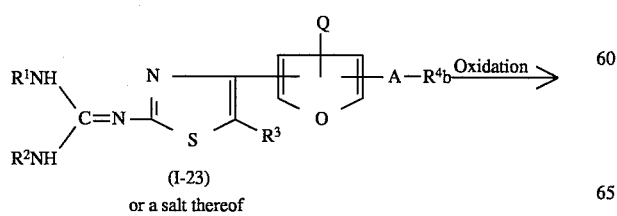
(I-23)
or a salt thereof
-continued
Process 21
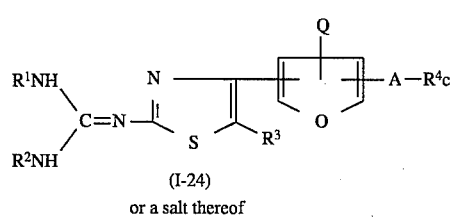
(I-24)
or a salt thereof Process 22
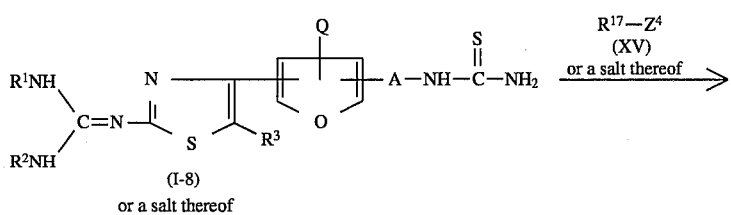
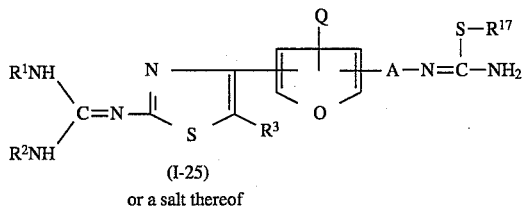
Process 23
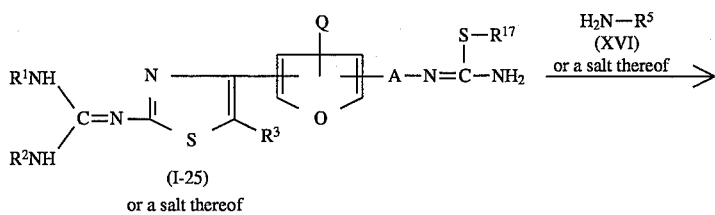
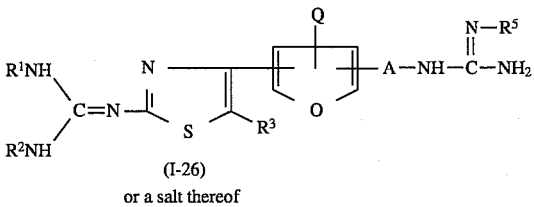
Process 24
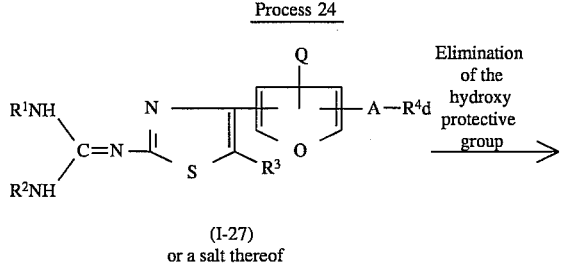
-continued
Process 24
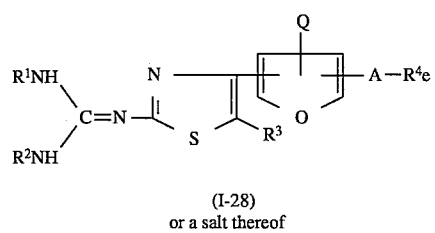

Process 25

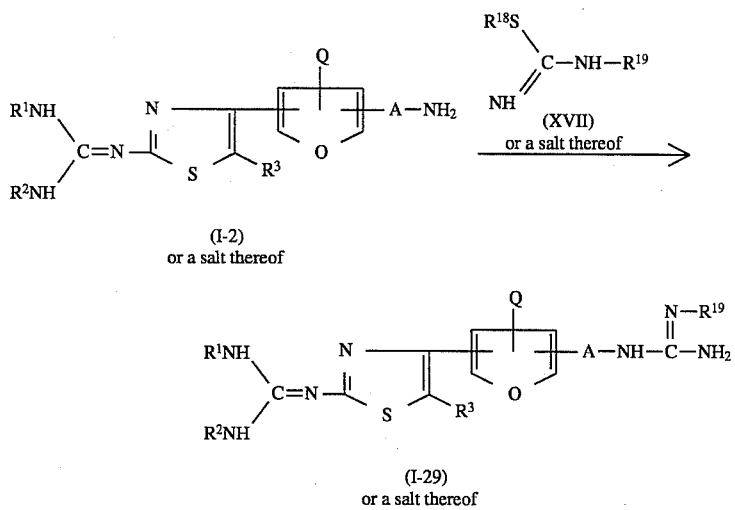

(I-2) or a salt thereof (I-29) or a salt thereof

Process 26

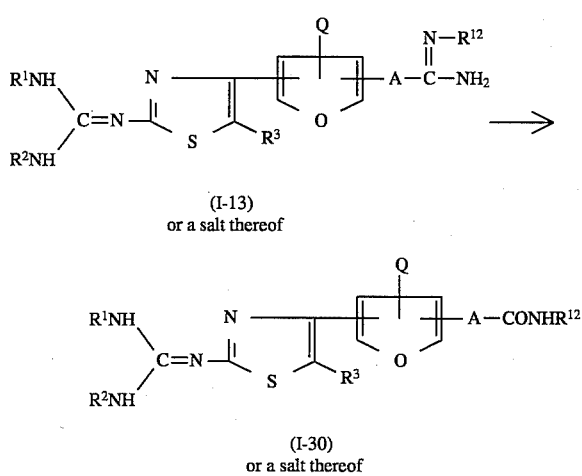

(I-13) or a salt thereof (I-30) or a salt thereof wherein $R^1$, $R^2$, $R^3$, $R^4$, $R^5$, $R^6$, X, A and Q are each as defined above, $R^4a$ is acylamino, $R^4b$ is acylamino including thio, $R^4c$ is acylamino including sulfinyl, $R^4d$ is acylamino including protected hydroxy, $R^4e$ is acylamino including hydroxy, $R^6a$ is amino which may have suitable substituent(s) or lower alkoxy, $R^7$ is lower alkyl or aryl, $R^8$ is amino-protective group, $R^9$, $R^{11}$, $R^{13}$, $R^{15}$, $R^{17}$ and $R^{18}$ are each lower alkyl, $R^{10}$ is protected hydroxy, $R^{14}$ is hydrogen or lower alkyl, $R^{16}$ is heterocyclic group, $X^1$ is S or O, $Z^1$, $Z^2$, $Z^3$ and $Z^4$ are each acid residue, and $A^1$ is lower alkylene or bond.

In the above and subsequent descriptions of the present specification, suitable examples of the various definitions to be included within the scope of the invention are explained in detail in the following.

The term "lower" is intended to mean a group having 1 to 6 carbon atom(s) preferably 1 to 4 carbon atom(s), unless otherwise provided.

Suitable "lower alkyl" and lower alkyl moiety in the term "lower alkylthio" may be a straight or branched one such as methyl, ethyl, propyl, isopropyl, butyl, isobutyl, tert-butyl, pentyl, hexyl or the like, in which the preferable one is $C_1$-$C_4$ alkyl and the more preferable one is methyl or ethyl.

Suitable "lower alkoxy" may be methoxy, ethoxy, propoxy, isopropoxy, butoxy, isobutoxy, tert-butoxy, pentyloxy, hexyloxy or the like, in which the preferable one is $C_1$-$C_4$ alkoxy, the more preferable one is $C_1$-$C_2$ alkoxy and the most preferable one is methoxy.

Suitable "acyl" and the acyl moiety in the term "acylamino" may include carbamoyl, thiocarbamoyl, sulfamoyl, an aliphatic acyl, an aromatic acyl, a heterocyclic acyl and an aliphatic acyl substituted with aromatic or heterocyclic group(s) derived from carbamic, sulfonic, carboxylic or carbonic acids and their thio acids.

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, isopropoxycarbonyl, butoxycarbonyl, tert-butoxycarbonyl, etc.), lower alkenoyl (e.g. acryloyl, methacryloyl, crotonoyl, etc.), ($C_3$-$C_7$)cycloalkanecarbonyl (e.g. cyclohexanecarbonyl, etc.), lower alkoxalyl (e.g. methoxalyl, ethoxalyl, etc.), lower alkanoylcarbonyl (e.g. pyruvoyl, etc.), lower alkanoyloxy(lower)alkanoyl (e.g. acetoxyacetyl, acetoxypropionyl, etc.,), and the like.

The aromatic acyl may include aroyl (e.g. benzoyl, nitrobenzoyl, toluoyl, xyloyl, etc.), arenesulfonyl (e.g. benzenesulfonyl, tosyl, etc.), and the like.

The heterocyclic acyl may include heterocyclic carbonyl (e.g. furoyl, thenoyl, nicotinoyl, 1-oxonicotinoyl, isonicotinoyl, thiazolylcarbonyl, thiadiazolylcarbonyl, tetrazolylcarbonyl, morpholinocarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with suitable substituent(s) such as hydroxy, amino, carboxy, lower alkyl (e.g. methyl, ethyl, propyl, isopropyl, butyl, pentyl, hexyl, etc.), lower alkenyl (e.g. vinyl, allyl, etc.), halogen (e.g. chloro, bromo, iodo, fluoro), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), heterocyclic(lower)alkylthio (e.g. furylmethylthio, thiazolylmethylthio, etc.), heterocyclic(lower)alkylsulfinyl e.g. furylmethylsulfinyl, thiazolylmethylsulfinyl, etc.), nitro, acyl as mentioned above, protected amino in which the amino protective moiety may be the same as those herein, aryl (e.g. phenyl, etc,), aroyl (e.g. benzoyl, etc.), aryloxy (e.g. benzyloxy, tolyloxy, etc.), protected hydroxy such as acyloxy, for example, lower alkanoyloxy (e.g. formyloxy, acetyloxy, propionyloxy, butyryloxy, isobutyryloxy, valeryloxy, isovaleryloxy, pivaloyloxy, hexanoyloxy, etc.), lower alkylamino (e.g. methylamino, ethylamino, etc.), amino-protective group as aftermentioned, and the like, and the preferable acyl having such substituent(s) may be lower alkoxy(lower)alkanoyl (e.g. methoxyacetyl, ethoxyacetyl, etc.), lower alkanoyloxy(lower)alkanoyl (e.g. acetoxyacetyl, etc.), N-lower alkylcarbamoyl (e.g. N-methylcarbamoyl, N-ethylcarbamoyl, N-isopropylcarbamoyl, etc.), aroylthiocarbamoyl (e.g. benzoylthiocarbamoyl, etc.), etc.

Suitable "heterocyclic group" and heterocyclic moiety in the term "heterocyclic amino" may include saturated or unsaturated, monocyclic or polycyclic heterocyclic group containing at least one hetero-atom such as an oxygen, sulfur, nitrogen atom and the like. Especially preferably heterocyclic group may be 5 or 6-membered aromatic heteromonocyclic group (e.g. pyrrolyl, imidazolyl, pyrazolyl, triazolyl, tetrazolyl, pyridyl, pyrazinyl, pyrimidinyl, pyridazinyl, thiazolyl, thiadiazolyl, etc.), 5- or 6-membered aliphatic heteromonocyclic group (e.g. morpholinyl, pyrrolidinyl, imidazolidinyl, pyrazolidinyl, piperidyl, piperazinyl, etc.), unsaturated condensed heterocyclic group containing 1 to 2 sulfur atom(s) and 1 to 3 nitrogen atom(s) (e.g. benzothiazolyl, benzoisothiazolyl, benzothiadiazolyl, etc.), and the like. Thus defined heterocyclic moiety may have suitable substituent(s) such as amino, oxo, halogen as chloro, lower alkyl as defined above, and the like. Preferable example of such a group is thiazolyl having lower alkyl (e.g. 4-methylthiazolyl, etc.).

Suitable "amino-protective group" may include ar(lower)alkyl such as benzyl, benzhydryl, phenethyl and the like, and acyl as mentioned above.

Suitable hydroxy-protective group in the term "protected hydroxy" may include aforesaid acyl, ar(lower)alkyl (e.g. benzyl, trityl, etc.) lower alkoxy(lower)alkyl (e.g. methoxymethyl, 1-methyl-1-methoxyethyl, methoxypropyl, etc.), tetrahydropyranyl, lower alkyl as aforementioned and the like.

Suitable "acid residue" may include halogen such as chloro, bromo, fluoro and iodo.

Suitable "lower alkylene" may be straight or branched one such as methylene, ethylene, trimethylene, propylene, tetramethylene, pentamethylene, hexamethylene, and the like, in which the preferable one is $C_1$–$C_4$ alkylene and the most preferable one is methylene and ethylene.

Suitable "lower alkylisothioureido" may include 2-lower alkylisothioureido such as 2-methylisothioureido, 2-ethylisothioureido, 3-propylisothioureido, and the like.

Suitable "amino which may have suitable substituent(s)" is conventional one used in a pharmaceutical field and may include amino, mono or di(lower)alkylamino (e.g. methylamino, dimethylamino, ethylamino, butylamino, etc.), lower alkenylamino (e.g. vinylamino, propenylamino etc.), lower alkynylamino (e.g. ethynylamino, propynylamino, etc.), hydroxy(lower)alkylamino (e.g. hydroxymethylamino, hydroxyethylamino, hydroxypropylamino, etc.), lower alkoxy(lower)alkylamino (e.g. methoxymethylamino, etc.), mono or di(lower)alkylamino(lower)alkylamino (e.g. methylaminomethylamino, dimethylaminoethylamino, etc.), and the like.

Suitable "acylamino including thio" may include acylamino as mentioned above, in which the optional carbon atom of the acyl moiety is replaced by a thio group, for example, heterocyclic(lower)alkylthio(lower)alkanoylamino such as 5- or 6-membered aromatic heteromonocyclic(lower)alkylthio(lower)alkanoylamino (e.g. furylmethylthioacetylamino, thiazolylmethylthioacetylamino, etc.), and the like.

Suitable "acylamino including sulfinyl" may include acylamino as mentioned above, in which the optional carbon atom of the acyl moiety is replaced by a sulfinyl group, for example, heterocyclic(lower)alkylsulfinyl(lower)alkanoylamino such as 5- or 6-membered aromatic heteromonocyclic(lower)alkylsulfinyl(lower)alkanoylamino (e.g. furylmethylsulfinylacetylamino, thiazolylmethylsulfinylacetylamino, etc.), and the like.

Suitable "acylamino including protected hydroxy" may include acylamino as mentioned above which is substituted by a protected hydroxy as exemplified above, for example, protected hydroxy(lower)alkylureido such as lower alkanoyloxy(lower)alkylureido (e.g. acetyloxyethylureido, etc.), and the like.

Suitable "acylamino including hydroxy" may include acylamino as mentioned above which is substituted by hydroxy such as hydroxy(lower)alkylureido (e.g. hydroxyethylureido, etc.), and the like.

Suitable "aryl" may include phenyl, tolyl, xylyl, mesityl, cumenyl, naphthyl, and the like, in which the preferred one is $C_6$–$C_{10}$ aryl.

Suitable "lower alkoxy(lower)alkyl" may include methoxymethyl, methoxyethyl, methoxypropyl, ethoxyethyl, 1-methyl-1-methoxyethyl, and the like.

Suitable "lower alkenyl" may include vinyl, 1-propenyl, allyl, 1-butenyl, 2-butenyl, 2-pentenyl, and the like, preferably one having 2 to 4 carbon atoms, in which the most preferred one is allyl.

Suitable "lower alkynyl" may include ethynyl, 1-propynyl, 2-propynyl, 3-butynyl, and the like, preferably one having 2 to 4 carbon atoms, in which the most preferred one is 2-propynyl.

Suitable "cyclo(lower)alkyl" may include cyclopropyl, cyclobutyl, cyclopentyl, cyclohexyl, and the like.

"Heterocyclic(lower)alkyl" means lower alkyl as mentioned above which is substituted by a heterocyclic group such as those exemplified above, and tile preferred example may include pyridyl(lower)alkyl such as pyridylmethyl, pyridylethyl, and the like.

Suitable "hydroxy(lower)alkyl" may include hydroxymethyl, hydroxyethyl, hydroxypropyl, and the like.

Suitable pharmaceutically acceptable salts of the object compound (I) are conventional non-toxic salts and include an organic acid addition salt [e.g. formate, acetate, trifluoroacetate, maleate, tartrate, methanesulfonate, benzenesulfonate, toluenesufonate, etc.], an inorganic acid addition salt [e.g. hydrochloride, hydrobromide, sulfate, phosphate, etc.], a salt with an acidic amino acid [e.g. aspartic acid salt, glutamic acid salt, etc.], and the like.

With respect to the salt of the compound (I-1) to (I-30) in the Process 1 to 26, it is to be noted that these compounds are included within the scope of the compound (I), and accordingly the suitable examples of the salts of these compounds are to be referred to those as exemplified for the object compound (I).

Particularly, the preferred embodiments of $R^1$, $R^3$, $R^4$, A and Q are as follows.

$R^1$ is ethyl;
  propyl;
  butyl;
  hexyl;
  lower alkoxy(lower)alkyl (e.g. methoxyethyl, ethoxyethyl,
  methoxypropyl, etc.);
  lower alkenyl (e.g. allyl, etc.);
  lower alkynyl (e.g. propynyl, etc.);
  cyclo(lower)alkyl (e.g. cyclohexyl, etc.);
  pyridyl(lower)alkyl (e.g. pyridylethyl, etc.); or
  hydroxy(lower)alkyl (e.g. hydroxyethyl, etc.);

$R^3$ is hydrogen;

$R^4$ is amino;
  acylamino such as ureido, lower alkanoylamino (e.g. acetylamino, etc.), lower alkoxycarbonylamino (e.g. methoxycarbonylamino, etc.) and lower alkanoyloxy(lower)alkanoylamino (e.g. acetoxyacetylamino, etc.);
  hydroxy(lower)alkanoylamino (e.g. hydroxyacetylamino, etc.); or
  2-cyano-3-lower alkylguanidino (e.g. 2-cyano-3-methylguanidino, etc.);

A is lower alkylene (e.g. methylene, etc.); and

Q is hydrogen; or
  lower alkyl (e.g. methyl, etc.).

The processes for preparing the object compounds (I) of the present invention are explained in detail in the following.

Process 1

The object compound (I) or a salt thereof can be prepared by reacting the compound (II) or a salt thereof with the compound (III).

This reaction is usually conducted in a conventional solvent which does not adversely influence the reaction such as ethyl acetate, dichloromethane, chloroform, carbon tetrachloride, tetrahydrofuran, N,N-dimethylformamide, N,N-dimethylacetamide, dioxane, water, alcohol [e.g. methanol, ethanol, etc.], acetic acid, formic acid, etc. or a mixture thereof.

The reaction temperature is not critical and the reaction is usually conducted under cooling to heating.

Process 2

The object compound (I-2) or a salt thereof can be prepared by subjecting the compound (I-1) or a salt thereof to deacylation.

Suitable method for this deacylation reaction may include conventional one such as hydrolysis, reduction or the like. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as tri(lower)alkylamine (e.g. trimethylamine, triethylamine, etc.), picoline, N-methylpyrrolidine, N-methylmorpholine, 1,5-diazabicyclo-[4.3.0]non-5-one, 1,4-diazabicyclo[2.2.2]octane, 1,5-diazabicyclo[5.4.0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and the reaction is usually carried out at ambient temperature or under warming or heating.

Process 3

The object compound (I-1) or a salt thereof can be prepared by reacting the compound (I-2) or a salt thereof with an acylating agent.

The compound (I-2) may be used in the form of its conventional reactive derivative at the amino group.

The acylating agent can be represented by the compound of the formula:

$$R^{20}-OH$$

in which $R^{20}$ is acyl as defined above and its conventional reactive derivative at the hydroxy group.

The suitable example may be an acid halide (e.g. acid chloride, etc.), an acid anhydride, an activated amide, an activated ester, and the like.

In case the acyl group to be introduced is a carbamoyl type acyl, the acylating agent is usually used in the form of cyanate or isocyanate.

The reaction is usually carried out in a conventional solvent such as water, alcohol [e.g. methanol, ethanol, etc.], acetone, dioxane, acetonitrile, chloroform, dichloromethane, ethylene chloride, tetrahydrofuran, ethyl acetate, N,N-dimethylformamide, N,N-dimethylacetamide, pyridine, acetic acid or any other organic solvent which does not adversely influence the reaction. These conventional solvents may also be used in a mixture with water.

The reaction temperature is not critical, and the reaction is usually carried out under cooling to warming.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

Process 4

The object compound (I-3) or a salt thereof can be prepared by reacting the compound (I-2) or a salt thereof with the compound (IV).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 5

The object compound (I-4) or a salt thereof can be prepared by reacting the compound (I-3) or a salt thereof with the compound (V).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

In case that the compound (V) is liquid, it can be also used as a solvent.

The reaction temperature is not critical, and the reaction is usually carried out at ambient temperature or under warming or heating.

Process 6

The object compound (I-6) or a salt thereof can be prepared by subjecting the compound (I-5) or a salt thereof to hydrolysis reaction.

This reaction is usually carried out in a conventional manner for transforming nitrile to amide.

This reaction is usually carried out in a conventional solvent which does not adversely influence the reaction such as water, alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 7

The object compound (I-8) or a salt thereof can be prepared by subjecting the compound (I-7) or a salt thereof to elimination reaction of the amino-protective group.

This reaction can be carried out in substantially the same manner as Process 2, and therefore the reaction mode and reaction conditions [e.g. solvent, reaction temperature, etc.] of this reaction are to be referred to those as explained in Process 2.

Process 8

The object compound (I-9) or a salt thereof can be prepared by reacting the compound (I-8) or a salt thereof with the compound (VI).

This reaction can be carried out in substantially the same manner as Process 1, and therefore the reaction mode and reaction conditions [e.g. solvent, reaction temperature, etc.] of this reaction are to be referred to those as explained in Process 1.

Process 9

The object compound (I-10) or a salt thereof can be prepared by reacting the compound (I-2) or a salt thereof with the compound (VII).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 10

The object compound (I-12) or a salt thereof can be prepared by reacting the compound (I-11) or a salt thereof with the compound (VIII).

This reaction is usually carried our in the presence of dry hydrogen chloride gas.

This reaction is usually carried out in a conventional solvent such as alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical, and the reaction is usually carried out under cooling to heating.

The object compound (I-12) can be used as a starting compound of Process 15 mentioned hereinbelow with or without isolation.

Process 11

The object compound (I-13) or a salt thereof can be prepared by reacting the compound (I-12) or a salt thereof with the compound (IX).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 12

The object compound (I-14) or a salt thereof can be prepared by subjecting the compound (I-11) or a salt thereof to reduction.

The reduction may include, for example, reduction with an alkali metal borohydride (e.g. sodium borohydride, etc.), and the like.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out under cooling to heating.

Process 13

The object compound (I) or a salt thereof can be prepared by reacting the compound (X) or a salt thereof with the compound (XI) or a salt thereof.

This reaction can be carried out in substantially the same manner as Process 5, and therefore the reaction mode and reaction conditions [e.g. solvent, reaction temperature, etc.] of this reaction are to be referred to those as explained in Process 5.

Process 14

The object compound (I-15) or a salt thereof can be prepared by subjecting the compound (I-12) or a salt thereof to hydrolysis.

This reaction is usually carried out in a conventional solvent such as a mixture of water and alcohol [e.g. methanol, etc.] or any other solvent which does not adversely influence the reaction.

The reaction temperature is not critical, and the reaction is usually carried out under cooling to heating.

Process 15

The object compound (I-16) or a salt thereof can be prepared by subjecting the compound (I-15) or a salt thereof to amidation.

This reaction is usually carried out in the presence of ammonia gas.

This reaction is usually carried out in a conventional solvent such as alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction.

The reaction temperature is not critical, and the reaction is usually carried out at ambient temperature or under warming or heating.

Process 16

The object compound (I-18) or a salt thereof can be prepared by reacting the compound (I-17) or a salt thereof with the compound (XII).

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 17

The object compound (I-19) or a salt thereof can be prepared by reacting the compound (XIII) or a salt thereof with hydrazine.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 18

The object compound (I-20) or a salt thereof can be prepared by reacting the compound (I-19) or a salt thereof with S-(lower)alkylisothiourea or a salt thereof.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 19

The object compound (I-21) or a salt thereof can be prepared by subjecting the compound (I-20) or a salt thereof to ring closure.

This reaction is usually carried out in the presence of ammonium hydride.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 20

The object compound (I-22) or a salt thereof can be prepared by reacting the compound (I-2) or a salt thereof with the compound (XIV) or a salt thereof.

This reaction is usually carried out in a conventional solvent such as water, acetone, dioxane, acetonitrile, chloroform, dichloromethane, ethylene chloride, tetrahydrofuran, ethyl acetate, N,N-dimethylformamide, N,N-dimethylacetamide, pyridine or any other organic solvent which does not adversely influence the reaction. These conventional solvents may also be used in a mixture with water.

The reaction temperature is not critical, and the reaction is usually carried out under cooling to warming.

The reaction may also be carried out in the presence of an inorganic or organic base such as an alkali metal bicarbonate, tri(lower)alkylamine (e.g. triethylamine, etc.), pyridine, N-(lower)alkylmorpholine, N,N-di(lower)alkylbenzylamine, or the like.

Process 21

The object compound (I-24) or a salt thereof can be prepared by oxidizing the compound (I-23) or a salt thereof.

The oxidizing agent to be used in this reaction may include an inorganic peracid or a salt thereof (e.g. periodic acid, persulfuric acid, or sodium or potassium salt thereof, etc.), an organic peracid or a salt thereof (e.g. perbenzoic acid, m-chloroperbenzoic acid, performic acid, peracetic acid, chloroperacetic acid, trifluoroperacetic acid, or sodium or potassium salt thereof, etc.), ozone hydrogen peroxide, urea-hydrogen peroxide, N-halosuccinimide (e.g. N-bromosuccinimide, N-chlorosuccinimide, etc.), hypochlorite compound (e.g. tert-butyl hypochlorite, etc.), permanganate (e.g. potassium permanganate, etc.), or any other conventional oxidizing agent which can oxidide a sulfide group to a sulfoxide group.

The present reaction can also be carried out in the presence of a compound comprising Group Vb or VIb metal in the Periodic Table of elements, for example, tungstic acid, molybdic acid, vanadic acid, etc., or an alkali or an alkaline earth metal salt thereof.

The present oxidation reaction is usually carried out in a conventional solvent which does not adversely influence the reaction such as water, acetic acid, chloroform, methylene chloride, acetone, methanol, ethanol, tetrahydrofuran, N,N-dimethylformamide or a mixture thereof.

The reaction temperature is not critical, and the reaction is usually carried out under cooling to at ambient temperature.

Process 22

The compound (I-25) or a salt thereof can be prepared by reacting the compound (I-8) or a salt thereof with the compound (XV) or a salt thereof.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Process 23

The object compound (I-26) or a salt thereof can be prepared by reacting the compound (I-25) or a salt thereof with the compound (XVI) or a salt thereof.

This reaction can be carried out in substantially the same manner as Process 5, and therefore the reaction mode and reaction conditions [e.g. solvent, reaction temperature, etc.] of this reaction are to be referred to those as explained in Process 5.

Process 24

The object compound (I-28) or a salt thereof can be prepared by subjecting the compound (I-27) or a salt thereof to elimination reaction of the hydroxy-protective group.

This reaction can be carried out in substantially the same manner as Process 2, and therefore the reaction mode and reaction conditions [e.g. solvent, reaction temperature, etc.] of this reaction are to be referred to those as explained in Process 2.

Process 25

The object compound (I-29) or a salt thereof can be prepared by reacting the compound (I-2) or a salt thereof with the compound (XVII) or a salt thereof.

This reaction is usually carried out in a conventional solvent which does not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

The reaction may also be carried out in the presence of an inorganic or organic base such as tri(lower)alkylamine (e.g. triethylamine, etc.), or the like.

Process 26

The object compound (I-30) or a salt thereof can be prepared by subjecting the compound (I-13) or a salt thereof to hydrolysis.

The hydrolysis is preferably carried out in the presence of a base or an acid.

This reaction is usually carried out in a conventional solvent which dose not adversely influence the reaction such as alcohol [e.g. methanol, ethanol, propanol, etc.], tetrahydrofuran, dioxane, dimethyl sulfoxide, N,N-dimethylformamide or a mixture thereof.

The reaction temperature is not critical, and the reaction is usually carried out at ambient temperature or under warming or heating.

Among the starting compounds, some of them are new and such compounds can be prepared by the methods of Preparation mentioned below and by any process known in the art for preparing structurally analogous compounds thereto.

The compounds obtained by the above Processes 1 to 26 can be isolated and purified by a conventional method such as pulverization, recrystallization, column chromatography, reprecipitation or the like.

It is to be noted that each of the object compound (I) may include one or more stereoisomer such as optical isomer(s) and geometrical isomer(s) due to asymmetric carbon atom(s) and double bond(s) and all such isomers and mixture thereof are included within the scope of this invention.

Furthermore, with regard to the compound (I), it is to be noted that the following formula (A) is well known to lie to tautomeric relation with the following formula (B), and accordingly, it is to be understood that both of the isomers are substantially the same.

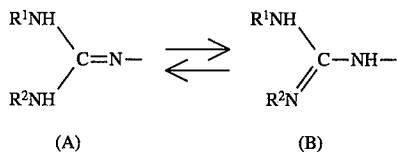

(A)        (B)

Accordingly, the both of the tautomeric forms are clearly included within the scope of the present invention. In the present specification, the object and starting compounds including the group of such tautomeric isomers are represented by using one of the expressions.

The new furylthiazole derivatives (I) and pharmaceutically acceptable salts thereof possess antiulcer activity and $H_2$-receptor antagonism, and are useful for a therapeutic treatment of gastritis, ulcer (e.g. gastric ulcer, duodenal ulcer, anastomotic ulcer, etc.), Zollinger-Ellison syndrome, reflux esophagitis, upper gastrointestinal bleeding, and the like.

And further, the compound (I) and pharmaceutically acceptable salts thereof of the present invention possess high antimicrobial activity against pathogenic microorganisms such as Campylobacter pyloridis, helicobacter pyloridis, and the like, which is a gram-negative bacillus that has recently been found beneath the mucus gel of the human stomach.

For therapeutic purpose, the compound (I) and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral or parenteral administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating ulcer. In general, amounts between 0.1 mg/body and about 1,000 mg/body may be administered per day.

In order to illustrate the usefulness of the object compound (I), the pharmacological test data of some representative compounds of the compound (I) are shown in the following.

Test Compounds (a) 4-(5-Acetylaminomethylfuran-2-yl)-2-[(amino)(n-butylamino)methyleneamino] thiazole (b) 4-(5-Acetylaminomethylfuran-2-yl)-2-[(amino)(n-hexylamino)methyleneamino] thiazole (c) 4-(5-Acetylaminomethylfuran-2-yl)-2-[(amino)-(2-methoxyethylamino)methyleneamino]thiazole (d) 4-(5-Acetylaminomethylfuran-2-yl)-2-[(amino)-[2-(2-pyridyl)ethylamino]methyleneamino]thiazole (e) 4-(5-Acetylaminomethylfuran-2-yl)-2-[(amino)-)allylamino)methyleneamino]thiazole Test A ($H_2$-receptor antagonism in isolated guinea-pig atrium):

Test Method

The atrial strip isolated from guinea-pig was suspended under an initial tension 0.3 to 0.6 g in an organ bath containing Tyrode solution at 30°C., aerated 95% $O_2$-5% $CO_2$ gas. The beating rate and amplitude of contraction of the atrium were recorded by means of a transducer and a polygraph. Histamine ($1\times10^{-6}$ g/ml) was added to the bathing fluid and the increase in beating rate after dosing was measured. Addition of test compounds ($1\times10^{-6}$ g/ml) was made 30 minutes after washing out histamine. Inhibitory effect of test compound was calculated by comparing histamine-induced increases in beating rate before and 30 minutes after dosing with the test compounds.

| Test Result | |
| --- | --- |
| Test Compound | $H_2$ Antagonism (%) |
| (b) | 78.5 |

Test B (Gastric secretion from lumen perfused stomach in anesthetized rats):

Test Method

Male Sprague-Dawley rats weighing about 250 g were used. Rats were deprived of food but allowed free access to water for 24 hours. The animals were anesthetized with 1.25 g/kg urethane intraperitoneally. The abdomen was opened and the gastric lumen was perfused with saline throughout the experiment. The perfusate was titrated by an autotitrator with 25 mM sodium hydroxide as a titrant. Gastric secretion was stimulated by intravenous infusion with histamine (3 mg/kg/hr). After reaching plateau, test compound (1 mg/kg)

was given intravenously. Drug effect was expressed as maximal inhibition by acid output.

| Test Result | |
|---|---|
| Test Compound | Inhibition (%) |
| (c) | 69 |

Test C (Anti-microbial activity):
Test Method

In vitro antimicrobial activity was determined by the agar dilution method. Test strain was precultured in Brucella broth Agar containing 5% horse serum at 37° C. for 3 days, and $10^4$ cfu/ml were inoculated with a multipoint replicater onto Brucella agar plus 5% lysed horse blood plate containing serial 2-fold dilutions of each drug at 37° C. for 3 days. Incubation was carried out in an atmosphere of 10% $CO_2$. MIC was read after incubation as the lowest drug concentration that inhibited macroscopic colonial growth.

| | Test Results MIC (µg/ml) | | |
|---|---|---|---|
| | | Test compound | |
| Test strain | (b) | (d) | (e) |
| *Campylobacter pyloridis* 8008 | 0.1 | 0.78 | 0.78 |

Test D (Inhibition of HCl-aspirin ulcer):
Test Method

Seven male Sprague-Dawley rats, aged 6 weeks and weighing about 200 g were used per group for the study on HCl-aspirin ulcer after the fast for 24 hours. Each of the test compounds (32 mg/kg) suspended in 0.1% methylcellulose solution was administered orally 30 minutes before aspirin administration. Aspirin, suspended in 0.1% methylcellulose solution containing 0.2N HCl, was administered orally at a dose of 200 mg/kg/10 ml. One hour later, the animals were sacrificed and their stomachs were removed. The stomach was then fixed with 2% formalin. The length of ulcers was measured for each animal, and percentage of inhibition was calculated by comparing the mean length of ulcers (mm) in the test animals with that in the control animals.

| Test Result | |
|---|---|
| Test Compound | Inhibition (%) |
| (a) | 86.9 |

The following Preparations and Examples are given for the purpose of illustrating the present invention in more detail.

Preparation 1

A suspension of 4-(5-acetylaminomethylfuran-2-yl)-2-thioureidothiazole (12.6 g) and methyl iodide (7.2 g) in methanol (200 ml) was refluxed for 5.5 hours. The solvent was removed under reduced pressure. The residue was washed with ethyl acetate to afford 4-(5-acetylaminomethylfuran-2-yl)-2-(2-methylisothioureido)thiazole hydriodide (15.7 g).

mp: 188° to 190° C. (dec.)
IR (Nujol): 3280, 1630, 1580 $cm^{-1}$
NMR (DMSO-$d_6$, δ): 1.87 (3H, s), 2.60 (3H, s), 4.29 (2H, d, J=5.5 Hz), 6.36 (1H, d, J=3.3 Hz), 6.89 (1H, d, J=3.3 Hz), 7.31 (1H, s), 8.38 (1H, t, J=5.5 Hz), 9.67 (1H, br)

Preparation 2

A suspension of 2-acetamidomethyl-5-chloroacetyl-3-methylfuran (24.8 g) and thiourea (8.2 g) in ethanol (250 ml) was stirred at room temperature for 2 hours. The resulting precipitate was collected by filtration and then dissolved in water (200 ml). The mixture was alkalized with an aqueous potassium carbonate solution. The resulting precipitate was collected by filtration to afford 4-(5-acetylaminomethyl-4-methylfuran-2-yl)-2-aminothiazole (16.7 g).

mp: 218° to 220° C.
IR (Nujol): 3350, 3150, 1640, 1620 $cm^{-1}$
NMR (DMSO-$d_6$, δ): 1.81 (3H, s), 1.98 (3H, s), 4.20 (2H, d, J=5.4 Hz), 6.34 (1H, s), 6.60 (1H, s), 7.08 (2H, s), 8.26 (1H, t, J=5.4 Hz)

Preparation 3

Benzoyl chloride (8.9 g) was added slowly to a solution of sodium thiocyanate (5.5 g) in acetone (200 ml) under refluxing. The mixture was refluxed for 15 minutes 4-(5-acetylaminomethyl-4-methylfuran-2-yl)-2-aminothiazole (13.2 g) was added to the mixture under refluxing. The mixture was refluxed for 8 hours. The resulting precipitate was collected by filtration. The precipitate was washed with water and then acetone to afford 4-(5-acetylaminomethyl-4-methylfuran-2-yl)-2-benzoylthioureidothiazole (15.1 g).

mp: 215° to 217° C. (dec.)
IR (Nujol): 3290, 1630 $cm^{-1}$
NMR (DMSO-$d_6$, δ): 1.74 (3H, s), 1.83 (3H, s), 4.25 (2H, d, J=5.4 Hz), 6.65 (1H, s), 7.34 (1H, s), 7.57 (2H, t, J=7.3 Hz), 7.70 (1H, dt, J=1.5 and 7.3 Hz), 8.02 (2H, dd, J=7.3 and 1.5 Hz), 8.33 (1H, t, J=5.4 Hz), 12.21 (1H, br), 14.22 (1H, br)

Preparation 4

An aqueous sodium hydroxide solution (3.5 g in 30 ml) was added to a suspension of 4-(5-acetylaminomethyl-4-methylfuran-2-yl)-2-benzoylthioureidothiazole (15.0 g) in methanol (200 ml).

The mixture was heated at 60° C. for 9 hours. The solvent was removed under reduced pressure. Water (200 ml) was added. The solution was neutralized with 6N hydrogen chloride solution. The resulting precipitate was collected by filtration to afford 4-(5-acetylaminomethyl-4-methylfuran-2-yl)-2-thioureidothiazole (10.9 g).

mp: 222° to 225° C.
IR (Nujol): 1620 $cm^{-1}$
NMR (DMSO-$d_6$, δ): 1.82 (3H, s), 2.01 (3H, s), 4.23 (2H, d, J=5.4 Hz), 6.54 (1H, s), 7.10 (1H, s), 8.20 (1H, br), 8.28 (1H, t, J=5.4 Hz), 8.76 (1H, br), 11.76 (1H, s)

Preparation 5

The following compound was obtained according to a similar manner to that of Preparation 1. 4-(5-Acetylaminomethyl-4-methylfuran-2-yl)-2-(2-methylisothioureido)thiazole hydriodide (7.5 g).

mp: 172° to 173° C. (dec.)
IR (Nujol):3220, 1590 $cm^{-1}$
NMR (DMSO-$d_6$, δ): 1.82 (3H, s), 2.01 (3H, s), 2.52 (3H, s), 4.23 (2H, d, J=5.4 Hz), 6 74 (1H, s), 7.20 (1H, s), 8.30 (1H, t, J=5.4 Hz), 9.38 (1H, br)

EXAMPLE 1

A suspension of 4-(5-acetylaminomethylfuran-2-yl)-2-(2-methylisothioureido) thiazole hydroiodide (2.0 g) and n-butylamine (5 ml) in ethanol (40 ml) was refluxed for 42 hours. The solvent was removed under reduced pressure and the residue was dissolved in water (100 ml). The mixture was alkalized to pH 10 with a saturated aqueous potassium carbonate solution and then extracted with a mixture of ethyl acetate (200 ml) and tetrahydrofuran (50 ml). The extract was dried with magnesium sulfate and then evaporated. Recrystallization from ethyl acetate afforded 4-(5-acetylaminomethylfuran-2-yl)-2-[(amino)(n-butylamino) methyleneamino]thiazole (0.30 g).

mp: 147° to 148° C.

IR (Nujol): 3460, 3310, 3200, 1640, 1610 cm$^{-1}$

NNR (DMSO-d$_6$, δ): 0.91 (3H, t, J=7.0 Hz), 1.29–1.48 (4H, m), 3.16 (2H, q, J=7.0 Hz), 4.26 (2H, d, J=5.5 Hz), 6.30 (1H, d, J=3.1 Hz), 6.54 (1H, d, J=3.1 Hz), 6.77 (1H, s), 7.32 (2H, br), 8.34 (1H, t, J=5.5 Hz)

Anal. Calcd. for C$_{15}$H$_{21}$N$_5$O$_2$S: C 53.71, H 6.31, N 20.88
Found: C 53.99, H 6.41, N 20.68

EXAMPLE 2

The following compounds were obtained according to a similar manner to that of Example 1.

(1) 4-(5-Acetylaminomethylfuran-2-yl)-2-[(amino)(n-hexylamino)methyleneamino]thiazole mp: 138° to 139° C.

IR (Nujol): 3460, 3220, 1630, 1590 cm$^{-1}$

NHR (DMSO-d$_6$, δ): 0.87 (3H, t, J=6.4 Hz), 1.05–1.60 (8H, m ), 1.85 (3H, s), 3.16 (2H, q, J=6.4 Hz), 4.26 (2H, d, J=5.5 Hz), 6 29 (1H, d, J=3.1 Hz), 6.54 (1H, d, J=3.1 Hz), 7.06 (1H, s), 7.32 (2H, s), 8.34 (1H, t, J=5.5 Hz)

Anal. Calcd. for C$_{17}$H$_{25}$N$_5$O$_2$S. 1/2H$_2$O: C 54.82, H 7.04, N 18.80 Found: C 55.21, H 7.17, N 18.81

(2) 4-(5-Acetylaminomethylfuran-2-yl)-2-[(amino)(2-methoxyethylamino)methyleneamino]thiazole mp: 137° to 138° C.

IR (Nujol): 3480, 3300, 3100, 1650, 1590 cm$^{-1}$

NMR (DMSO-d$_6$, δ): 1.85 (3H, s), 3.28–3.45 (4H, m), 4.26 (2H, d, J=5.5 Hz), 6.30 (1H, d, J=3.2 Hz), 6 59 (1H, d, J =3.2 Hz), 6.78 (1H, s), 7.05–7.60 (12H, br), 8.34 (1H, t, J=5.5 Hz)

(3) 4-(5-Acetylaminomethylfuran-2-yl )-2-[(amino) [2-(2-pyridyl)ethylamino]methyleneamino]thiazole mp: 67° to 68° C.

IR (Nujol):3520, 3380, 3280, 1630, 1590 cm$^{-1}$

NMR (DMSO-d$_6$, δ): 1.85 (3H, s), 2.98 (2H, t, J=6.9 Hz), 3.58 (2H, q, J=6.9 Hz), 4.26 (2H, d, J=5.5 Hz), 6.29 (1H, d, J=3.1 Hz), 6.53 (1H, d, J=3.1 Hz), 6.77 (1H, s), 7.23 (1H, ddd, J=1.1 Hz, 4.9 Hz and 7.6 Hz), 7.32 (1H, br, d, J=7.6 Hz), 7.40 (2H, br), 7.72 (1H, dt, J=1.1 Hz and 7.6 Hz), 8.35 (1H, t, J=5.5 Hz), 8.51 (1H, ddd, J=0.8 Hz, 1.1 Hz and 4.9 Hz), Anal. Calcd. for C$_{18}$H$_{20}$N$_6$O$_2$S. H$_2$O: C 51.42, H 5.75, N 19.99 Found: C 51.38, H 5.82, N 19.89

(4) 4-(5-Acetylaminomethylfuran-2-yl )-2-[(amino)(allylamino)methyleneamino]thiazole mp: 160° to 161° C.

IR (Nujol): 3380, 3180, 3100, 1650, 1600 cm$^{-1}$

NMR (DMSO-d$_6$, δ): 1.85 (3H, s), 3.84 (2H, t, J=5.3 Hz), 4.26 (2H, d, J=5.5 Hz), 5.12 (1H, dd, J=1.6 Hz and 10.3 Hz), 5.22 (1H, dd, J=1.6 Hz and 17.2 Hz), 5.81–6.00 (1H, m), 6.30 (1H, d, J=3.2 Hz), 6.57 (1H, d, J=3.2 Hz), 6.80 (1H, s), 7.43 (2H, s), 8.34 (1H, t, J=5.5 Hz), Anal. Calcd. for C$_{14}$H$_{17}$N$_5$O$_2$S: C 52.65, H 5.37, N 21.93 Found: C 52.85, H 5.63, N 21.62

(5) 4-(5-Acetylaminomethylfuran-2-yl)-2-[(amino)(cyclohexylamino)methyleneamino]thiazole mp: 154° to 155° C.

IR (Nujol): 3390, 3060, 1665, 1590 cm$^{-1}$

NMR (DMSO-d$_6$, δ): 1.30–1.90 (13H, m), 3.54 (1H, br), 4.26 (2H, d, J=5.5 Hz), 6.30 (1H, d, J=3.2 Hz), 6.53 (1H, d, J=3.2 Hz), 6.76 (1H, s), 7.26 (2H, br), 8.34 (1H, t, J=5.5 Hz)

(6) 4-(5-Acetylaminomethylfuran-2-yl )-2-[(amino)(methylamino)methyleneamino]thiazole mp: 188° to 189° C.

IR (Nujol): 3400, 3350, 1630, 1585 cm$^{-1}$

NMR (DMSO-d$_6$, δ): 1.85 (3H, s), 2.74 (3H, d, J=4.8 Hz), 4.26 (2H, d, J=5.5 Hz), 6.29 (1H, d, J=3.2 Hz), 6.60 (1H, d, J=3.2 Hz), 6.77 (1H, s), 7.42 (2H, br), 8.35 (1H, t, J=5.5 Hz)

Anal. Calcd. for C$_{12}$H$_{15}$N$_5$O$_2$S: C 49.13, H 5.15, N 23.87 Found: C 49.31, H 5.04, N 23.84

EXAMPLE 3

A solution of 4-(5-acetylaminomethylfuran-2-yl)-2-[(amino)(allylamino)methyleneamino]thiazole (4.77 g) and conc-hydrochloric acid (5 ml) in ethanol (100 ml) was refluxed for 33 hours. After cooling, the resulting precipitate was collected by filtration to afford 4-(5-aminomethylfuran-2-yl)-2-[(amino)(allylamino)methyleneamino]thiazole dihydrochloride (3.7 g).

mp: 259° to 260° C. (dec.)

IR (Nujol): 3230, 3170, 1680, 1630 cm$^{-1}$

NMR (DMSO-d$_6$, δ): 4.12 (4H, br), 5.25 (1H, dd, J=1.4 Hz and 10.4 Hz), 5.34 (1H, dd, J=1.4 Hz and 17.3 Hz), 5.87–6.01 (1H, m), 6.68 (1H, d, J=3.3 Hz), 6.95 (1H, d, J=3.3 Hz), 7.41 (1H, s), 8.30–9.30 (6H, br), 12.50–13.05 (1H, br),

EXAMPLE 4

The following compounds were obtained according to a similar manner to that of Example 3.

(1) 4-(5-Aminomethylfuran-2-yl)-2-[(amino)(2-methoxyethylamino)methyleneamino]thiazole dihydrochloride mp: 252° to 253° C. (dec.)

IR (Nujol): 3450, 3250, 1680, 1640, 1600 cm$^{-1}$

NMR (DMSO-d$_6$, δ): 3.35 (3H, s), 3.59 (4H, br), 4.13 (2H, br d, J=4.4 Hz), 6.70 (1H, d, J=3.2 Hz), 6.88 (1H, d, J=3.2 Hz), 7.41 (1H, s), 8.60–8.68 (5H, br), 9.40 (1H, br), 12.99 (1H, br)

(2) 4-(5-Aminomethylfuran-2-yl)-2-[(amino)(n-butylamino)methyleneamino]thiazole dihydrochloride mp: 270° to 276° C. (dec.)

IR (Nujol): 3410, 3340, 3080, 2700, 2620, 1700, 1640 cm$^{-1}$

NMR (DMSO-d$_6$, δ): 0.93 (3H, t, J=7.2 Hz), 1.31–1.63 (4H, m), 3.40 (2H, m), 4.12 (2H, br), 6.68 (1H, d, J=3.2 Hz), 6.92 (1H, d, J=3.2 Hz), 7.40 (1H, s), 8.63 (5H, br), 9.04 (1H, br), 12.80 (1H, br)

(3) 4-(5-Aminomethylfuran-2-yl)-2-[(amino)[2-(2-pyridyl)ethylamino]methyleneamino]thiazole trihydrochloride mp : 266° to 268° C. (dec.)

IR (Nujol): 3210, 1660, 1600 cm$^{-1}$

NMR (DMSO-d$_6$, δ): 3.34 (2H, t, J=4.9 Hz), 3.93 (2H, q, J=4.9 Hz), 4.14 (2H, q, J=5.5 Hz), 6.66 (1H, d, J=3.4 Hz), 6.91 (1H, d, J=3.4 Hz), 7.40 (1H, s), 7.76 (1H, m), 7.96 (1H, m), 8.33 (1H, m), 8.62–8.86 (6H, m), 9.13 (1H, br)

EXAMPLE 5

A solution of 4-(5-aminomethylfuran-2-yl)-2-[(amino)(allylamino)methyleneamino]thiazole dihydrochloride (1.5 g) and potassium cyanate (0.73 g) in water (30 ml) was stirred at room temperature for 4 hours. The resulting precipitate was collected by filtration. Recrystallization from a mixture of methanol and diisopropyl ether afforded 2-[(amino)(allylamino)methyleneamino]-4-(5-ureidomethylfuran-2-yl)thiazole hemi hydrochloride (0.50 g).

mp: 120° to 122° C. (dec.)

IR (Nujol): 3420, 3230, 3120, 1620 cm$^{-1}$

NMR (DMSO-d$_6$, δ): 3.94 (2H, br), 4.20 (2H, d, J=5.7 Hz), 5.18 (1H, dd, J=10.0 and 1.5 Hz), 5.26 (1H, dd, J=16.0 and 1.5 Hz), 5.59 (2H, s), 5.85–5.99 (1H, m), 6.28 (1H, d, J=3.2 Hz), 6.42 (1H, t, J=5.7 Hz), 6.69 (1H, d, J=3.2 Hz), 7.03 (1H, s), 7.97 (2H, br), Anal. Calcd. for C$_{13}$H$_{16}$N$_6$O$_2$S. 1/2HCl.H$_2$O: C 43.78, H 5.23, N 23.57 Found: C 44.03, H 5.07, N 23.59

EXAMPLE 6

The following compounds were obtained according to a similar manner to that of Example 5.

(1) 2-[(Amino)(2-methoxyethylamino)methyleneamino]-4-(5-ureidomethylfuran-2-yl)thiazole mp: 152° to 155° C. (dec.)

IR (Nujol): 3390, 3330, 3200, 3110, 1660, 1590 cm$^{-1}$

NMR (DMSO-d$_6$, δ): 3.30–3.45 (7H, m), 4.19 (2H, d, J=5.7 Hz), 5.57 (2H, s), 6.26 (1H, d, J=3.2 Hz), 6.38 (1H, t, J=5.7 Hz), 6.58 (1H, d, J=3.2 Hz), 6.78 (1H, s), 7.35 (2H, br)

Anal. Calcd. for C$_{13}$H$_{18}$N$_6$O$_3$S. 1/2H$_2$O: C 44.95, H 5.51, N 24.19, H$_2$O 2.59 Found: C 44.94, H 5.62, N 23.96, H$_2$O 2.88

(2) 2-[(Amino)(n-butylamino)methyleneamino]-4-(5-ureidomethylfuran-2-yl)thiazole mp: 123° to 124° C.

IR (Nujol): 3230, 1650, 1610 cm$^{-1}$

NMR (DMSO-d$_6$, δ): 0.91 (3H, t, J=7.0 Hz), 1.29–1.48 (4H, m), 3.16 (2H, q, J=6.3 Hz), 4.19 (2H, d, J=5.7 Hz), 5.56 (2H, s), 6.25 (1H, d, J=3.2 Hz), 6.37 (1H, t, J=5.7 Hz), 6.54 (1H, d, J=3.2 Hz), 6.76 (1H, s), 7.32 (2H, s)

Anal. Calcd. for C$_{14}$H$_{20}$N$_6$O$_2$S. 1/2H$_2$O: C 48.68, H 6.13, N 24.33, H$_2$O 2.61 Found : C 48.36, H 6.04, N 24.18, H$_2$O 2.81

(3) 2-[(Amino)[2-(2-pyridyl)ethylamino]methyleneamino]-4-(5-ureidomethylfuran-2-yl)thiazole mp : 127° to 128° C. (dec.)

IR (Nujol): 3430, 3310, 3200, 1640 cm$^{-1}$

NMR (DMSO-d$_6$, δ): 2.98 (2H, t, J=6.8 Hz), 3.58 (2H, q, J=6.8 Hz), 4.19 (2H, d, J=5.7 Hz), 5.56 (2H, s), 6.25 (1H, d, J=3.1 Hz), 6.38 (1H, t, J=5.7 Hz), 6.53 (1H, d, J=3.1 Hz), 6.76 (1H, s), 7.23 (1H, dd, J=7.6 Hz and 4.5 Hz), 7.32 (1H, br d, J=7.6 Hz), 7.40 (2H, s), 7.72 (1H, dt, J=7.6 Hz and 1.8 Hz), 8.51 (1H, br d, J=4.5 Hz)

Anal. Calcd. for C$_{17}$H$_{19}$N$_7$O$_2$.2H$_2$O: C 48.45, H 5.50, N 23.26, H$_2$O 8.55 Found: C 48.12, H 5.35, N 23.07, H$_2$O 8.77

EXAMPLE 7

The following compounds were obtained according to a similar manner to that of Example 1.

(1) 4-(5-Acetylaminomethyl-4-methylfuran-2-yl)-2-[(amino)(methylamino)methyleneamino]thiazole mp: 171° to 172° C.

IR (Nujol): 3400, 3260, 3120, 1630 cm$^{-1}$

NMR (DMSO-d$_6$, δ): 1.82 (3H, s), 2.00 (3H, s), 2.74 (3H, d, J=4.8 Hz), 4.22 (2H, d, J=5.4 Hz), 6.50 (1H, s), 6.73 (1H, s), 7.41 (2H, br), 8.27 (1H, t, J=5.4 Hz)

Anal. Calcd. for C$_{13}$H$_{17}$N$_5$O$_2$S. 1/10H$_2$O: C 50.50, H 5.61, N 22.65

Found: C 50.34, H 5.48, N 22.59

(2) 4-(5-Acetylaminomethyl-4-methylfuran-2-yl)-2-[(amino)-(2-methoxyethylamino)methyleneamino]thiazole mp: 152° to 154° C.

IR (Nujol): 3450, 3320, 3200, 3130, 1640, 1600 cm$^{-1}$

NMR (DMSO-d$_6$, δ): 1.82 (3H, s), 1.99 (3H, s), 3.30 (3H, s), 3.36 (2H, t, J=4.5 Hz), 3.43 (2H, q, J=4.5 Hz), 4.21 (2H, d, J=5.4 Hz), 6.49 (1H, s), 6.74 (1H, s), 7.35 (2H, br), 8.27 (1H, t, J=5.4 Hz)

Anal. Calcd. for C$_{15}$H$_{21}$N$_5$O$_3$S: C 51.27, H 6.02, N 19.93 Found: C 50.97, H 6.06, N 19.65

(3) 4-(5-Acetylaminomethylfuran-2-yl)-2-[(amino)(2-hydroxyethylamino)methyleneamino]thiazole mp: 181° to 182° C.

IR (Nujol): 3450, 3350, 3280, 1630, 1600 cm$^{-1}$

NMR (DMSO-d$_6$, δ): 1.85 (3H, s), 3.20–3.29 (2H, m), 3.47–3.55 (2H, m), 4.26 (2H, d, J=5.5 Hz), 4.87 (1H, t, J=5.0 Hz), 6.29 (1H, d, J=3.2 Hz), 6.61 (1H, d, J=3.2 Hz), 6.77 (1H, s), 7.34 (2H, br), 8.32 (1H, t, J=5.5 Hz)

EXAMPLE 8

The following compound was obtained according to a similar manner to that of Example 3.

4-(5-Aminomethylfuran-2-yl)-2-[(amino)(n-hexylamino)methyleneamino]thiazole dihydrochloride.

mp: 273° to 276° C.

IR (Nujol): 3310, 3250, 1700, 1640 cm$^{-1}$

NMR (DMSO-d$_6$, δ): 0.87, (3H, t, J=6.6 Hz), 1.20–1.50 (6H, m), 1.50–1.70 (1H, d, J=3.2 Hz), 3.37 (2H, m), 4.13 (2H, br), 6.68 (1H, d, J=3.2 Hz), 6.42 (1H, d, J=3.2 Hz), 7.40 (1H, s), 8.60 (4H, brs), 9.02 (1H, br), 12.80 (1H, br)

EXAMPLE 9

The following compound was obtained according to a similar manner to that of Example 5.

2-[(Amino)(n-hexylamino)methyleneamino]-4-(5-ureidomethylfuran- 2-yl)thiazole.

mp: 98° to 100° C.

IR (Nujol): 3320, 1640 cm$^{-1}$

NMR (DMSO-d$_6$, δ): 0.87 (3H, t, J=6.4 Hz), 1.10–1.40 (6H, m), 1.40–1.60 (2H, m), 3.16 (2H, q, J=5.7 Hz), 4.19 (2H, d, J=5.7 Hz), 5.56 (2H, s), 6.25 (1H, d, J=3.2 Hz), 6.38 (1H, t, J=5.7 Hz), 6.54 (1H, d, J=3.2 Hz), 6.76 (1H, s), 7.31 (2H, br)

Anal. Calcd. for C$_{16}$H$_{24}$N$_6$O$_2$S. 2/3H$_2$O: C 51.05, H 6.78, N 22.32 Found: C 51.14, H 6.80, N 22.50

EXAMPLE 10

A solution of acetoxyacetyl chloride (1.3 g) in dichloromethane (10 ml) was added slowly to a solution of 4-(5-aminomethylfuran-2-yl)-2-[(amino)(2-methoxyethylamino)methyleneamino]thiazole dihydrochloride (3.0 g) and triethylamine (2.0 g) in dichloromethane (40 ml) with cooling on an ice bath. The mixture was stirred for 8 hours with cooling on an ice bath. The solvent was removed under reduced pressure. The residue was suspended in water (100 ml). The mixture was alkalized with an aqueous potassium carbonate solution and then was extracted with a mixture of ethyl acetate (250 ml) and tetrahydrofuran (50 ml). The extract was dried with magnesium sulfate. The solvent was removed under reduced pressure. Recrystallization from a mixture of ethanol and water to afford 4-(5-acetoxyacetylaminomethylfuran-2-yl)-2-[(amino)(2-methoxyethylamino)methyleneamino]thiazole (2.4 g).

mp: 112° to 113° C.

IR (Nujol): 3350, 1750, 1660 cm$^{-1}$

NMR (DMSO-d$_6$, δ): 2.09 (3H, s), 3.30 (3H, s), 3.36 (2H, t, J=4.5 Hz), 3.43 (2H, q, J=4.5 Hz), 4.32 (2H, d, J=5.6 Hz), 4.49 (2H, s), 6.30 (1H, d, J=3.2 Hz), 6.59 (1H, d, J=3.2 Hz), 6.78 (1H, s), 7.35 (2H, br), 8.55 (1H, t, J=5.6 Hz)

Anal. Calcd. for C$_{16}$H$_{21}$N$_5$O$_5$S. 1/3H$_2$O: C 46.99, H 5.55, N 17.13 Found: C 47.17, H 5.45, N 16.82

EXAMPLE 11

The following compound was obtained according to a similar manner to that of Example 10.

2-[(Amino)(2-methoxyethylamino)methyleneamino]-4-(5-methoxycarbonylaminomethylfuran-2-yl)thiazole.

mp: 93° to 95° C.

IR (Nujol): 3310, 3200, 1700, 1660, 1590 cm$^{-1}$

NMR (DMSO-d$_6$, δ): 3.30–3.50 (7H, m), 3.56 (3H, s), 4.20 (2H, d, J=5.8 Hz), 6.28 (1H, d, J=3.2 Hz), 6.58 (1H, d, J=3.2 Hz), 6.77 (1H, s), 7.35 (2H, br), 7.69 (1H, t, J=5.8 Hz)

Anal. Calcd. for C$_{14}$H$_{19}$N$_5$O$_4$S. 1/2H$_2$O: C 46.40, H 5.56, N 19.32 Found: C 46.38, H 5.42, N 19.18

EXAMPLE 12

The following compounds were obtained according to a similar manner to that of Example 1.

(1) 4-(5-Acetylaminomethylfuran-2-yl)-2-[(amino)(ethylamino)methyleneamino]thiazole mp: 170° to 171° C.

IR (Nujol): 3470, 3280, 3100, 1650, 1600 cm$^{-1}$

NMR (DMSO-d$_6$, δ): 1.10 (3H, t, J=7.1 Hz), 1.85 (3H, s), 3.12–3.25 (2H, m), 4.26 (2H, d, J=5.5 Hz), 6.29 (1H, d, J=3.2 Hz), 6.56 (1H, d, J=3.2 Hz), 6.77 (1H, s), 7.38 (2H, br), 8.35 (1H, t, J=5.5 Hz)

Anal. Calcd. for C$_{13}$H$_{17}$N$_5$O$_2$S: C 50.80, H 5.57, N 22.78 Found: C 50.89, H 5.47, N 22.45

(2) 4-(5-Acetylaminomethylfuran-2-yl)-2-[(amino)(n-propylamino)(methyleneamino]thiazole mp: 155° to 156° C.

IR (Nujol): 3460, 3320, 3210, 1640, 1600 cm$^{-1}$

NMR (DMSO-d$_6$, δ): 0.91 (3H, t, J=7.3 Hz), 1.42–1.60 (2H, m), 1.85 (3H, s), 3.08–3.17 (2H, m), 4.26 (2H, d, J=5.5 Hz), 6.30 (1H, d, J=3.2 Hz), 6.55 (1H, d, J=3.2 Hz), 6.77 (1H, s), 7.33 (2H, br), 8.35 (1H, t, J=5.5 Hz)

(3) 4-(5-Acetylaminomethylfuran-2-yl)-2-[(amino)(2-ethoxyethylamino)methyleneamino]thiazole mp: 144° to 145° C.

IR (Nujol): 3460, 3300, 3100, 1650, 1590 cm$^{-1}$

NMR (DMSO-d$_6$, δ): 1.14 (3H, t, J=7.0 Hz), 1.85 (3H, s), 3.31–3.33 (2H, m), 3.43–3.53 (4H, m), 4.26 (2H, d, J=5.5 Hz), 6.29 (1H, d, J=3.2 Hz), 6.59 (1H, d, J=3.2 Hz), 6.78 (1H, s), 7.37 (2H, br), 8.34 (1H, t, J=5.5 Hz)

Anal. Calcd. for C$_{15}$H$_{21}$N$_5$O$_3$S: C 51.27, H 6.02, N 19.93 Found: C 51.30, H 6.15, N 19.88

(4) 4-(5-Acetylaminomethylfuran-2-yl)-2-[(amino)(3-methoxypropylamino)methyleneamino]thiazole mp: 135° to 136° C.

IR (Nujol): 3280, 3130, 1650, 1600 cm$^{-1}$

NMR (DMSO-d$_6$, δ): 1.66–1.79 (2H, m), 1.85 (3H, s), 3.16–3.23 (5H, m), 3.33–3.42 (2H, m), 4.26 (2H, d, J=5.5 Hz), 6.30 (1H, d, J=3.2 Hz), 6.56 (1H, d, J=3.2 Hz), 6.77 (1H, s), 7.37 (2H, br), 8.34 (1H, t, J=5.5 Hz)

Anal. Calcd. for C$_{15}$H$_{21}$N$_5$O$_3$S: C 51.27, H 6.02, 19.93 Found: C 51.29, H 6.07, N 19.79

EXAMPLE 13

The mixture of 2-acetylaminomethyl-5-chloroacetylfuran (2.7 g) and N-propargylamidinothiourea (2.5 g) in ethanol (20.0 ml) was stirred for 3 hours at 70° C..

To the reaction mixture was added an ethyl acetate (20.0 ml) and isolated precipitate was collected by filtration.

The precipitate was recrystallized from a mixture of methanol and diisopropyl ether to give 4-(5-acetylaminomethyl-furan-2-yl )-2-[(amino)(propargylamino)methyleneamino]thiazole hydrochloride (1.55 g).

mp: 209° to 210° C.

IR (Nujol): 3280, 3180, 1630 cm$^{-1}$

NMR (D$_2$O, δ): 2.07 (3H, s), 2.91 (1H, t, J=2.4 Hz), 4.10 (2H, d, J=2.4 Hz), 4.40 (2H, s), 6.38 (1H, d, J=3.3 Hz), 6.53 (1H, d, J=3.3 Hz), 7.12 (1H, s)

Anal. Calcd. for C$_{14}$H$_{15}$N$_5$O$_2$S. HCl. 1/3H$_2$O: C 46.73, H 4.67, N 19.46, Cl 9.85, H$_2$O 1.67 Found: C 46.96, H 4.69, N 19.15, Cl 9.81, H$_2$O 1.71

EXAMPLE 14

A suspension of 4-(5-acetoxyacetylaminomethylfuran-2-yl)-2-[(amino)(2-methoxyethylamino)methyleneamino] thiazole (1.6 g) in a saturated methanolic ammonia solution (50 ml) was stirred for 3 hours with cooling on an ice bath. The solvent was removed under reduced pressure. Recrystallization from methanol afforded 2-[(amino)(2- methoxyethylamino)methyleneamino]-4-(5-hydroxyacetylaminomethylfuran-2-yl)thiazole (0.9 g).

mp: 104° to 105° C.

IR (Nujol): 3620, 3430, 3110, 1660, 1620 cm$^{-1}$

NMR (DMSO-d$_6$, δ): 3.30 (3H, s), 3.36 (2H, t, J=4.5 Hz), 3.43 (2H, q, J=4.5 Hz), 3.85 (2H, d, J=5.9 Hz), 4.32 (2H, d, J=6.0 Hz), 5.49 (1H, t, J=5.9 Hz), 6.28 (1H, d, J=3.2 Hz), 6.58 (1H, d, J=3.2 Hz), 6.77 (1H, s), 7.34 (2H, br), 8.19 (1H, t, J=6.0 Hz)

Anal. Calcd. for C$_{14}$H$_{19}$N$_5$O$_4$S. 7/4H$_2$O: C 43.68, H 5.89, N 18.19 Found: C 43.87, H 5.83, N 18.17

EXAMPLE 15

A mixture of 2-[(amino)(allylamino)methyleneamino]-4-(5-ureidomethylfuran-2-yl)thiazole hemi hydrochloride (950 mg) in water (20 ml) was alkalized with 20% aqueous potassium carbonate solution to pH 10. The mixture was stirred at room temperature for 1 hour and then was extracted with a mixture of ethylacetate (150 ml) and tetrahydrofuran (50 ml). The extract was dried with magnesium sulfate. The solvent was removed under reduced pressure. Recrystallization from a mixture of methanol and water afforded 2-[(amino)(allylamino)methyleneamino]-4-(5-ureidomethylfuran-2-yl)thiazole (650 mg).

mp: 88° to 89° C.

IR (Nujol): 3430, 3220, 1630, 1600 cm$^{-1}$

NMR (DMSO-d$_6$, δ) 3.84 (2H, t, J=5.4 Hz), 4.19 (2H, d, J=5.7 Hz), 5.12 (1H, dd, J=10.3 and 1.7 Hz), 5.22 (1H, dd, J=17.2 and 1.7 Hz), 5.56 (2H, s), 5.81–6.00 (1H, m), 6.25 (1H, d, J=3.2 Hz), 6.38 (1H, t, J=5.7 Hz), 6.57 (1H, d, J=3.2 Hz), 6.79 (1H, s), 7.43 (2H, br)

Anal. Calcd. for C$_{13}$H$_{16}$N$_6$O$_2$S. H$_2$O: C 46.14, H 5.36, N 24.84 Found: 46.02, H 5.34, N 24.80

EXAMPLE 16

The following compounds were obtained according to a similar manner to that of Example 3.

(1) 4-(5-Aminomethylfuran-2-yl)-2-[(amino)(methylamino)methyleneamino] thiazole dihydrochloride mp: 269° to 270° C. (dec.)
IR (Nujol): 3300, 1700, 1640 cm$^{-1}$
NMR (DMSO-d$_6$, δ): 3.16 (3H, d, J=4.9 Hz), 4.12 (2H, br), 6.68 (1H, d, J=3.3 Hz), 7.05 (1H, d, J=3.3 Hz), 7.41 (1H, s), 8.63–8.90 (6H, br), 12.91 (1H, br)

(2) 4-(5-Aminomethylfuran-2-yl)-2-[(amino)(ethylamino)methyleneamino]thiazole dihydrochloride mp: 275° to 277° C.

IR (Nujol): 3310, 1700, 1640 cm$^{-1}$

NMR (DMSO-d$_6$, δ): 1.21 (3H, t, J=7.1 Hz), 3.30∝3.50 (2H, m), 4.12 (2H, br), 6.68 (1H, d, J=3.3 Hz), 6.96 (1H, d, J=3.3 Hz), 7.40 (1H, s), 8.64 (5H, br), 8.97 (1H, br)

(3) 4-(5-Aminomethylfuran-2-yl)-2-[(amino)(n-propylamino)methyleneamino]thiazole dihydrochloride mp : 272° to 274° C. (dec.)

(Nujol): 3450, 3270, 1680, 1630 cm$^{-1}$

NMR (DMSO-d$_6$, δ): 0.96 (3H, t, J=7.3 Hz), 1.53–1.67 (2H, m), 3.34–3.42 (2H, m), 4.12 (2H, br), 6.69 (1H, d, J=3.2 Hz), 6.94 (1H, d, J=3.2 Hz), 7.42 (1H, s), 8.70 (5H, br s), 9.08 (1H, br), 12.89 (1H, br)

(4) 4-(5-Aminomethylfuran-2-yl)-2-[(amino)(2-ethoxyethylamino)methyleneamino] thiazole dihydrochloride mp: 266° to 268° C. (dec.)

IR (Nujol): 3300, 3250, 1700, 1640 cm$^{-1}$

NMR (DMSO-d$_6$, δ): 1.13 (3H, t, J=7.0 Hz), 3.48–3.62 (6H, m), 4.12 (2H, br), 6.69 (1H, d, J=3.2 Hz), 6.91 (1H, d, J=3.2 Hz), 7.41 (1H, s), 8.61–8.68 (5H, br), 9.34 (1H, br), 13.01 (1H, br)

(5) 4-(5-Aminomethylfuran-2-yl)-2-[(amino)(3-methoxypropylamino)methyleneamino]thiazole dihydrochloride mp: 263° to 265° C. (dec.)

IR (Nujol): 3300, 3090, 1690, 1640 cm$^{-1}$

NMR (DMSO-d$_6$, δ): 1.82–1.91 (2H, m), 3.24 (3H, s), 3.40–3.49 (4H, m), 4.14 (2H, br), 6.69 (1H, d, J=3.3 Hz), 6.95 (1H, d, J=3.3 Hz), 7.41 (1H, s), 8.66 (5H, br), 9.09 (1H, br), 12.83 (1H, br)

EXAMPLE 17

The following compounds were obtained according to a similar manner to that of Example 5.

(1) 2-[(Amino)(ethylamino)methyleneamino]-4-(5-ureidomethylfuran-2-yl)thiazole mp: 184° to 185° C.

IR (Nujol): 3320, 1630 cm$^{-1}$

NMR (DMSO-d$_6$, δ): 1.10 (3H, t, J=7.1 Hz), 3.12–3.25 (2H, m) 4.19 (2H, d, J=5.7 Hz), 5.56 (2H, s), 6.25 (1H, d, J=3.2 Hz), 6.38 (1H, t, J=5.7 Hz), 6.55 (1H, d, J=3.2 Hz), 6.76 (1H, s), 7.38 (2H, br)

Anal. Calcd. for C$_{12}$H$_{16}$N$_6$O$_2$S. 1/2H$_2$O: C 45.41, H 5.40, N 26.48 Found: C 45.31, H 5.49, N 26.40

(2) 2-[(Amino)(n-propylamino)methyleneamino]-4-(5-ureidomethylfuran- 2-yl)thiazole mp: 173° to 174° C.

IR (Nujol): 3430, 3350, 3120, 1630, 1600 cm$^{-1}$

NHR (DMSO-d$_6$, δ): 0.92 (3H, t, J=7.3 Hz), 1.42–1.60 (2H, m), 3.08–3.17 (2H, m), 4.19 (2H, d, J=5.7 Hz), 5.57 (2H, s), 6.25 (1H, d, J=3.2 Hz), 6.38 (1H, t, J=5.7 Hz), 6.54 (1H, d, J=3.2 Hz), 6.76 (1H, s), 7.33 (2H, br s)

Anal. Calcd. for C$_{13}$H$_{18}$N$_6$O$_2$S. 1/10H$_2$O: C 48.16, H 5.66, N 25.92 Found: C 48.14, H 5.81, N 25.69

(3) 2-[(Amino)(3-methoxypropylamino)methyleneamino]-4-(5-ureidomethylfuran-2-yl)thiazole mp: 164° to 165° C.

(Nujol): 3370, 3300, 3250, 3130, 1660, 1640, 1610 cm$^{-1}$

NMR (DMSO-d$_6$, δ): 1.66–1.79 (2H, m), 3.16–3.24 (5H, m), 3.36–3.45 (2H, m), 4.19 (2H, d, J=5.7 Hz), 5.56 (2H, s), 6.25 (1H, d, J=3.2 Hz), 6.38 (1H, t, J=5.7 Hz), 6.56 (1H, d, J=3.2 Hz), 6.77 (1H, s), 7.38 (2H, br)

Anal. Calcd. for C$_{14}$H$_{20}$N$_6$O$_3$S. 1/10H$_2$O: C 47.47, H 5.75, N 23.73 Found: C 47.38, H 5.69, N 23.42

(4) 2-[(Amino)(2-ethoxyethylamino)methyleneamino]-4-(5-ureidomethylfuran-2-yl)thiazole mp: 174° to 175° C.

IR (Nujol): 3330, 3180, 1650, 1620 cm$^{-1}$

NMR (DMSO-d$_6$, δ): 1.14 (3H, t, J=7.0 Hz), 3.34–3.53 (6H, m), 4.19 (2H, d, J=5.7 Hz), 5.57 (2H, s), 6.25 (1H, d, J=3.2 Hz), 6.38 (1H, t, J=5.7 Hz), 6.59 (1H, d, J=3.2 Hz), 6.77 (1H, s), 7.36 (2H, br)

Anal. Calcd. for C$_{14}$H$_{20}$N$_6$O$_3$S: C 47.71, H 5.72, N 23.85 Found: C 47.39, H 5.99, N 23.55

EXAMPLE 18

A solution of 4-(5-aminomethylfuran-2-yl)-2-[(amino)(3-methoxypropylamino)methyleneamino]thiazole (1.0 g), triethylamine (800 mg) and dimethyl N-cyanodithioiminocarbonate (460 mg) in N,N-dimethylformamide (20 ml) was heated at 70° C. for 4.5 hours. After cooling, 30% ethanolic methylamine solution (20 ml) was added and the mixture was stirred for 24 hours at room temperature. The solvent was removed under reduced pressure. The residue was dissolved in water (50 ml) and tetrahydrofuran (50 ml). The mixture was alkalized with 20% aqueous potassium carbonate solution to pH 10 and then was extracted with ethyl acetate (200 ml). The extract was dried with magnesium sulfate. The solvent was removed under reduced pressure. The residue was chromatographed on a silica gel column eluting with chloroform: methanol=20:1. The solvent was removed under reduced pressure and the residue was crystallized from ethyl acetate. Recrystallization from a mixture of methanol and diisopropyl ether afforded 2-[(amino)(3-methoxypropylamino)methyleneamino]-4-[5-(2-cyano-3-methylguanidino)methylfuran-2yl]thiazole (270 mg).

mp: 129° to 131° C.

IR (Nujol): 3400, 3260, 3120, 2170, 1670, 1630 cm$^{-1}$

NMR (DMSO-d$_6$, δ): 1.66–1.79 (2H, m), 2.71 (3H, d, J=4.6 Hz), 3.17–3.24 (5H, m), 3.36–3.42 (2H, m), 4.34 (2H, d, J=5.6 Hz), 6.31 (1H, d, J=3.2 Hz), 6.58 (1H, d, J=3.2 Hz), 6.77 (1H, s), 7.14 (1H, q, J=4.6 Hz), 7.39 (2H, br), 7.48 (1H, t, J=5.6 Hz)

Anal. Calcd. for C$_{16}$H$_{22}$N$_8$O$_2$S. 1/10H$_2$O: C 48.99, H 5.70, N 28.57 Found: C 48.77, H 5.73, N 28.29

EXAMPLE 19

The following compounds were obtained according to a similar manner to that of Example 18.

(1) 2-[(Amino)(methylamino)methyleneamino]-4-[5-(2-cyano-3-methylguanidino)methylfuran-2-yl]thiazole mp: 110° to 111° C. (dec.)

IR (Nujol): 3380, 3230, 2170, 1655 cm$^{-1}$

NMR (DMSO-d$_6$, δ): 2.71 (3H, d, J=4.7 Hz), 2.74 (3H, d, J=4.9 Hz), 4.34 (2H, d, J=5.6 Hz), 6.31 (1H, d, J=3.2 Hz), 6.61 (1H, d, J=3.2 Hz), 6.77 (1H, s), 7.13 (1H, q, J=4.7 Hz), 7.35–7.50 (3H, br)

Anal. Calcd. for C$_{13}$H$_{16}$N$_8$OS: C 46.98, H 4.85, N 33.71 Found: C 46.85, H 4.89, N 33.46

(2) 2-[(Amino)(ethylamino)methyleneamino]-4-[5-(2-cyano-3-methylguanidino)methylfuran-2-yl]thiazole mp: 172° to 173° C.

IR (Nujol): 3440, 3360, 3250, 2150, 1630, 1600 cm$^{-1}$

NMR (DMSO-$d_6$, δ): 1.11 (3H, t, J=7.1 Hz), 2.71 (3H, d, J=4.6 Hz), 3.12–3.25 (2H, m), 4.34 (2H, d, J=5.7 Hz), 6.31 (1H, d, J=3.2 Hz), 6.57 (1H, d, J=3.2 Hz), 6.76 (1H, s), 7.13 (1H, q, J=4.6 Hz), 7.38 (2H, br), 7.48 (1H, t, J=5.7 Hz)

Anal. Calcd. for $C_{14}H_{18}N_8OS \cdot 1/10H_2O$: C 48.29, H 5.27, N 32.18 Found: C 48.32, H 5.30, N 31.89

(3) 2-[(Amino)(n-propylamino)methyleneamino]-4-[5-(2-cyano-3-methylguanidino)methylfuran-2-yl]thiazole mp: 189° to 190° C.

IR (Nujol):3490, 3440, 3220, 2150, 1630, 1600 cm$^{-1}$

NMR (DMSO-$d_6$, δ): 0.92 (3H, t, J=7.3 Hz), 1.42–1.60 (2H, m), 2.71 (3H, d, J=4.7 Hz), 3.08–3.18 (2H, m), 4.34 (2H, d, J=5.7 Hz), 6.31 (1H, d, J=3.2 Hz), 6.56 (1H, d, J=3.2 Hz), 6.76 (1H, s), 7.13 (1H, q, J=4.7 Hz), 7.33 (2H, br), 7.47 (1H, t, J=5.7 Hz)

(4) 2-[(Amino)(n-butylamino)methyleneamino]-4-[5-(2-cyano-3-methylguanidino)methylfuran-2-yl]thiazole mp: 190° to 191° C.

IR (Nujol): 3480, 3400, 3230, 2150, 1650 cm$^{-1}$

NMR (DMSO-$d_6$, δ): 0.91 (3H, t, J=6.9 Hz) 1.26–1.52 (4H, m), 2.71 (3H, d, J=4.6 Hz), 3.12–3.21 (2H, m), 4.34 (2H, d, J=5.7 Hz), 6.31 (1H, d, J=3.2 Hz), 6.55 (1H, d, J=3.2 Hz), 6.76 (1H, s), 7.13 (1H, q, J=4.6 Hz), 7.32 (2H, br), 7.47 (1H, t, J=5.7 Hz)

Anal. Calcd. for $C_{16}H_{22}N_8OS$: C 51.32, H 5.92, N 29.92 Found: C 50.90, H 6.09, N 29.82

(5) 2-[(Amino)(allylamino)methyleneamino]-4-[5-(2-cyano-3-methylguanidino)methylfuran-2-yl]thiazole mp: 166° to 167° C.

IR (Nujol): 3420, 3200, 2140, 1630, 1600 cm$^{-1}$

NMR (DMSO-$d_6$, δ): 2.71 (3H, d, J=4.7 Hz), 3.80–3.90 (2H, m), 4.34 (2H, d, J=5.7 Hz), 5.11 (1H, dd, J=1.7 and 10.2 Hz), 5.22 (1H, dd, J=1.7 and 17.2 Hz), 5.81–5.97 (1H, m), 6.31 (1H, d, J=3.2 Hz), 6.59 (1H, d, J=3.2 Hz), 6.79 (1H, s), 7.13 (1H, q, J=4.7 Hz), 7.35–7.50 (3H, br)

Anal. Calcd. for $C_{15}H_{18}N_8OS \cdot 1/4H_2O$: C 49.64, H 5.14, N 30.88 Found: C 49.71, H 5.08, N 30.73

We claim:

1. A compound of the formula:

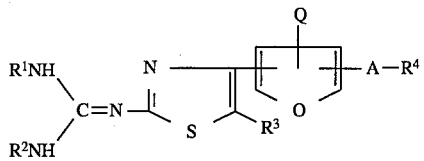

wherein $R^1$ is ethyl, propyl, butyl, hexyl, lower alkoxy(lower)alkyl, lower alkenyl, lower alkynyl, cyclo(lower) alkyl, heterocyclic(lower)alkyl selected from the group consisting of pyrrolyl(lower)alkyl, imidazolyl(lower)alkyl, pyrazolyl(lower)alkyl, triazolyl(lower)alkyl, tetrazolyl(lower)alkyl, pyridyl(lower)alkyl, pyrazinyl(lower)alkyl, pyrimidinyl(lower)alkyl, pyridazinyl(lower)alkyl, thiazolyl(lower)alkyl, thiadiazolyl(lower)alkyl, morpholinyl(lower)alkyl, pyrrolidinyl(lower)alkyl, imidazolidinyl(lower)alkyl, pyrazolidinyl(lower)alkyl, piperidyl(lower)alkyl, piperazinyl(lower) alkyl, benzothiazolyl(lower)alkyl, benzoisothiazolyl(lower)alkyl and benzothiadiazolyl(lower)alkyl or hydroxy(lower)alkyl, $R^2$ is hydrogen, $R^3$ is hydrogen or lower alkyl, $R^4$ is amino, acyl selected from the group consisting of carbamoyl, thiocarbamoyl, sulfamoyl, lower alkanoyl, lower alkanesulfonyl, lower alkoxycarbonyl, lower alkenoyl, ($C_3$–$C_7$) cycloalkanecarbonyl, lower alkoxalyl, lower alkanoylcarbonyl, lower alkanoyloxy(lower)alkanoyl, aroyl, arenesulfonyl, furoyl, thenoyl, nicotinoyl, 1-oxonicotinoyl, isonicotinoyl, thiazolylcarbonyl, thiadiazolylcarbonyl, tetrazolylcarbonyl, morpholinocarbonyl, phenyl(lower)alkanoyl, phenyl(lower)alkoxycarbonyl, phenoxy(lower) alkanoyl, thienylacetyl, imidazolylacetyl, furylacetyl, tetrazolylacetyl, thiazolylacetyl, thiadiazolylacetyl, thienylpropionyl, and thiadiazolylpropionyl, acylamino selected from the group consisting of carbamoylamino, thiocarbamoylamino, sulfamoylamino, lower alkanoylamino, lower alkanesulfonylamino, lower alkoxycarbonylamino, lower alkenoylamino, ($C_3$–$C_7$) cycloalkanecarbonylamino, lower alkoxalylamino, lower alkanoylcarbonylamino, lower alkanoyloxy(lower)alkanoylamino, aroylamino, arenesulfonylamino, furoylamino, thenoylamino, nicotinoylamino, 1-oxonicotinoylamino, isonicotinoylamino, thiazolylcarbonylamino, thiadiazolylcarbonylamino, tetrazolylcarbonylamino, morpholinocarbonylamino, phenyl(lower)alkanoylamino, phenyl(lower)alkoxycarbonylamino, phenoxy(lower)alkanoylamino, thienylacetylamino, imidazolylacetylamino, furylacetylamino, tetrazolylacetylamino, thiazolylacetylamino, thiadiazolylacetylamino, thienylpropionylamino and thiadiazolylpropionylamino, lower alkylisothioureido, heterocyclic amino selected from the group consisting of pyrrolylamino, imidazolylamino, pyrazolylamino, triazolylamino, tetrazolylamino, pyridylamino, pyrazinylamino, pyrimidinylamino, pyridazinylamino, thiazolylamino, thiadiazolylamino, morpholinylamino, pyrrolidinylamino, imidazolidinylamino, pyrazolidinylamino, piperidylamino, piperazinylamino, benzothiazolylamino, benzoisothiazolylamino and benzothiadiazolylamino, a heterocyclic group selected from the group consisting of pyrrolyl, imidazolyl, pyrazolyl, triazolyl, tetrazolyl, pyridyl, pyrazinyl, pyrimidinyl, pyridazinyl, thiazolyl, thiadiazolyl, morpholinyl, pyrrolidinyl, imidazolidinyl, pyrazolidinyl, piperidyl, piperazinyl, benzothiazolyl, benzoisothiazolyl and benzothiadiazolyl, or a group of the formula:

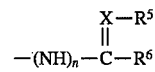

in which n is 0 or 1,

X is =CH— or =N—, $R^5$ is hydrogen, cyano, nitro or acyl, and $R^6$ is hydrogen, lower alkyl, lower alkylthio, lower alkoxy or amino which may have suitable substituent(s), and A is lower alkylene or —CONH—; or A—$R^4$ is a heterocyclic group as defined above, and Q is hydrogen or lower alkyl, and pharmaceutically acceptable salt thereof.

2. A compound of claim 1, wherein $R^1$ is lower alkoxy(lower)alkyl, lower alkenyl, lower alkynyl, cyclo(lower)alkyl, pyridyl(lower)alkyl or hydroxy(lower)alkyl, $R^4$ is acylamino or 2-cyano-3-lower alkylguanidino, and A is lower alkylene.

3. A compound of claim 2, wherein $R^4$ is ureido, lower alkanoylamino, lower alkoxycarbonylamino, lower alkanoyloxy(lower)alkanoylamino, hydroxy(lower)alkanoylamino or 2-cyano-3-lower alkylguanidino.

4. A compound of claim 3, wherein $R^1$ is methoxyethyl, ethoxyethyl, methoxypropyl, cyclohexyl, propenyl, propynyl, pyridylethyl or hydroxyethyl, $R^3$ is hydrogen, $R^4$ is ureido, acetylamino, methoxycarbonylamino, acetoxyacetylamino, hydroxyacetylamino or 2-cyano-3-methylguanidino, A is methylene, and Q is hydrogen or methyl.

5. A compound of claim 1, wherein $R^1$ is ethyl, propyl, butyl or hexyl, $R^4$ is acylamino or 2-cyano-3-lower alkylguanidino, and A is lower alkylene.

6. A compound of claim 5, wherein $R^4$ is ureido, lower alkanoylamino or 2-cyano-3-lower alkylguanidino.

7. A pharmaceutical composition which comprises, as an active ingredient, a compound of claim 1 or a pharmaceutically acceptable salt thereof in admixture with pharmaceutically acceptable carriers.

8. A method for the treatment of ulcer which comprises administering a compound of claim 1 or a pharmaceutically acceptable salt thereof to human or animals.

* * * * *